(12) United States Patent
Thambar et al.

(10) Patent No.: US 10,856,858 B2
(45) Date of Patent: Dec. 8, 2020

(54) HEART VALVE PROSTHESIS AND METHOD

(71) Applicant: Percutaneous Cardiovascular Solutions Pty Ltd, North Albury (AU)

(72) Inventors: Suku Thambar, New South Wales (AU); Martin Christopher Cook, Lane Cove (AU); Stefan Schreck, Duvall, WA (US); Stayajit Rohan Jayasinghe, Southport (AU)

(73) Assignee: Percutaneous Cardiovascular Solutions Pty Ltd, North Albury (AU)

( * ) Notice: Subject to any disclaimer, the term of this patent is extended or adjusted under 35 U.S.C. 154(b) by 0 days.

(21) Appl. No.: 16/226,185

(22) Filed: Dec. 19, 2018

(65) Prior Publication Data

US 2019/0125323 A1    May 2, 2019

Related U.S. Application Data

(63) Continuation of application No. 13/130,180, filed as application No. PCT/AU2009/001513 on Nov. 20, 2009, now Pat. No. 10,166,014.

(30) Foreign Application Priority Data

Nov. 21, 2008  (AU) ............................... 2008906045
Feb. 9, 2009   (AU) ............................... 2009900460

(51) Int. Cl.
  *A61F 2/24*    (2006.01)
  *A61B 17/00*   (2006.01)
  *A61F 2/848*   (2013.01)

(52) U.S. Cl.
  CPC ........ *A61B 17/0057* (2013.01); *A61F 2/2418* (2013.01); *A61F 2/2436* (2013.01);
  (Continued)

(58) Field of Classification Search
  CPC ................................ A61F 2/24; A61F 2/2436
  See application file for complete search history.

(56) References Cited

U.S. PATENT DOCUMENTS 3,671,979 A   6/1972  Moulopoulos
3,739,402 A   6/1973  Cooley et al.
(Continued)

FOREIGN PATENT DOCUMENTS

CN    101180010 A    5/2008
EP    0170262 A2     2/1986
(Continued)

OTHER PUBLICATIONS

Jeffrey S. Borer et al., "Contemporary Approach to Aortic and Mitral Regurgitation," Circulation 2003; 108:2432.
(Continued)

*Primary Examiner* — Matthew W Schall
(74) *Attorney, Agent, or Firm* — Klarquist Sparkman LLP

(57) ABSTRACT

A method of treating a heart includes radially expanding a housing component within a native atrioventricular valve. The housing component includes an atrial anchoring mechanism for deployment in the left atrium and ventricular prongs for engagement with native tissue in the left ventricle. The housing component also includes an interior passageway sized for receiving a valve component. After the housing component has been deployed, the valve component is radially expanded within the passageway of the housing component. The valve component includes three leaflets configured for allowing blood to flow from the left atrium to the left ventricle. After expansion within the housing component, the valve component may have an inflow end portion that protrudes above the housing component into the left atrium. The housing component and valve component are preferably collapsible for advancement through a patient's vasculature using one or more catheters.

22 Claims, 25 Drawing Sheets

(52) U.S. Cl.
CPC ............ *A61B 2017/0061* (2013.01); *A61B 2017/00575* (2013.01); *A61F 2/2457* (2013.01); *A61F 2002/8486* (2013.01); *A61F 2220/0008* (2013.01); *A61F 2220/0016* (2013.01); *A61F 2230/008* (2013.01); *A61F 2230/0054* (2013.01); *A61F 2230/0078* (2013.01); *A61F 2250/006* (2013.01)

(56) References Cited

U.S. PATENT DOCUMENTS

| | | |
|---|---|---|
| 3,898,701 A | 8/1975 | La Russa |
| 4,056,854 A | 11/1977 | Boretos et al. |
| 4,204,283 A | 5/1980 | Bellhouse et al. |
| 4,218,783 A | 8/1980 | Reul et al. |
| 4,225,980 A | 10/1980 | Ramos Martinez |
| 4,274,437 A | 6/1981 | Watts |
| 4,407,271 A | 10/1983 | Schiff |
| 4,666,442 A | 5/1987 | Arru et al. |
| 4,960,424 A | 10/1990 | Grooters |
| 5,078,739 A | 1/1992 | Martin |
| 5,197,980 A | 3/1993 | Gorshkov et al. |
| 5,207,707 A | 5/1993 | Gourley |
| 5,332,402 A | 7/1994 | Teitelbaum |
| 5,370,685 A | 12/1994 | Stevens |
| 5,397,347 A | 3/1995 | Cuilleron et al. |
| 5,397,351 A | 3/1995 | Pavcnik et al. |
| 5,405,381 A | 4/1995 | Olin |
| 5,554,184 A | 9/1996 | Machiraju |
| 5,554,186 A | 9/1996 | Guo et al. |
| 5,607,465 A | 3/1997 | Camilli |
| 5,628,792 A | 5/1997 | Lentell |
| 5,824,062 A | 10/1998 | Patke et al. |
| 5,861,029 A | 1/1999 | Evdokimov et al. |
| 5,861,030 A | 1/1999 | Rhee et al. |
| 5,908,451 A | 6/1999 | Yeo |
| 5,908,452 A | 6/1999 | Bokros et al. |
| 6,051,022 A | 4/2000 | Cai et al. |
| 6,086,612 A | 7/2000 | Jansen |
| 6,096,075 A | 8/2000 | Bokros et al. |
| 6,210,432 B1 | 4/2001 | Solem et al. |
| 6,287,334 B1 | 9/2001 | Moll et al. |
| 6,296,663 B1 | 10/2001 | Patke et al. |
| 6,312,464 B1 | 11/2001 | Navia |
| 6,332,893 B1 | 12/2001 | Mortier et al. |
| 6,358,277 B1 | 3/2002 | Duran |
| 6,419,695 B1 | 7/2002 | Gabbay |
| 6,445,630 B2 | 9/2002 | Ayadi et al. |
| 6,454,799 B1 | 9/2002 | Schreck |
| 6,458,153 B1 | 10/2002 | Bailey et al. |
| 6,482,228 B1 | 11/2002 | Norred |
| 6,485,489 B2 | 11/2002 | Teirstein et al. |
| 6,537,314 B2 | 3/2003 | Langberg et al. |
| 6,540,782 B1 | 4/2003 | Snyders |
| 6,569,196 B1 | 5/2003 | Vesely |
| 6,569,198 B1 | 5/2003 | Wilson et al. |
| 6,602,288 B1 | 8/2003 | Cosgrove et al. |
| 6,605,112 B1 | 8/2003 | Moll et al. |
| 6,616,684 B1 | 9/2003 | Vidlund et al. |
| 6,652,578 B2 | 11/2003 | Bailey et al. |
| 6,709,456 B2 | 3/2004 | Langberg et al. |
| 6,719,790 B2 | 4/2004 | Brendzel et al. |
| 6,723,038 B1 | 4/2004 | Schroeder et al. |
| 6,723,123 B1 | 4/2004 | Kazatchkov et al. |
| 6,730,121 B2 | 5/2004 | Ortiz et al. |
| 6,733,525 B2 | 5/2004 | Yang et al. |
| 6,752,813 B2 | 6/2004 | Goldfarb et al. |
| 6,764,510 B2 | 7/2004 | Vidlund et al. |
| 6,767,362 B2 | 7/2004 | Schreck |
| 6,790,231 B2 | 9/2004 | Liddicoat et al. |
| 6,797,002 B2 | 9/2004 | Spence et al. |
| 6,869,444 B2 | 3/2005 | Gabbay |
| 6,875,224 B2 | 4/2005 | Grimes |
| 7,004,958 B2 | 2/2006 | Adams et al. |
| 7,011,669 B2 | 3/2006 | Kimblad |
| 7,018,406 B2 | 3/2006 | Seguin et al. |
| 7,101,395 B2 | 9/2006 | Tremulis et al. |
| 7,160,322 B2 | 1/2007 | Gabbay |
| 7,175,656 B2 | 2/2007 | Khairkhahan |
| 7,217,287 B2 | 5/2007 | Wilson et al. |
| 7,226,467 B2 | 6/2007 | Lucatero et al. |
| 7,252,682 B2 | 8/2007 | Seguin |
| 7,276,078 B2 | 10/2007 | Spenser et al. |
| 7,291,168 B2 | 11/2007 | Macoviak et al. |
| 7,381,220 B2 | 6/2008 | Macoviak et al. |
| 7,393,360 B2 | 7/2008 | Spenser et al. |
| 7,404,824 B1 | 7/2008 | Webler et al. |
| 7,445,630 B2 | 11/2008 | Lashinski et al. |
| 7,556,145 B2 | 7/2009 | Elsner |
| 7,556,645 B2 | 7/2009 | Lashinski et al. |
| 7,559,936 B2 | 7/2009 | Levine |
| 7,678,145 B2 | 3/2010 | Vidlund et al. |
| 7,682,390 B2 | 3/2010 | Seguin |
| 7,758,596 B2 | 7/2010 | Oz et al. |
| 7,942,928 B2 | 5/2011 | Webler et al. |
| 8,052,751 B2 | 11/2011 | Aklog et al. |
| 8,172,856 B2 | 5/2012 | Eigler et al. |
| 8,348,963 B2 | 1/2013 | Wilson |
| 8,784,482 B2 | 7/2014 | Randert et al. |
| 8,932,348 B2 | 1/2015 | Solem et al. |
| 9,241,792 B2 | 1/2016 | Benichou et al. |
| 2001/0018611 A1 | 8/2001 | Solem et al. |
| 2002/0128708 A1 | 9/2002 | Northrup et al. |
| 2002/0198595 A1 | 12/2002 | Brendzel et al. |
| 2003/0014104 A1 | 1/2003 | Cribier |
| 2003/0023300 A1 | 1/2003 | Bailey et al. |
| 2003/0036791 A1 | 2/2003 | Philipp et al. |
| 2003/0036795 A1 | 2/2003 | Andersen et al. |
| 2003/0078654 A1 | 4/2003 | Taylor et al. |
| 2004/0019378 A1 | 1/2004 | Hlavka et al. |
| 2004/0024414 A1 | 2/2004 | Downing |
| 2004/0039442 A1 | 2/2004 | St. Goar et al. |
| 2004/0092858 A1 | 5/2004 | Wilson et al. |
| 2004/0093060 A1 | 5/2004 | Seguin et al. |
| 2004/0106976 A1 | 6/2004 | Bailey et al. |
| 2004/0117032 A1 | 6/2004 | Roth |
| 2004/0152947 A1 | 8/2004 | Schroeder et al. |
| 2004/0167539 A1 | 8/2004 | Kuehn et al. |
| 2004/0193259 A1 | 9/2004 | Gabbay |
| 2004/0210307 A1 | 10/2004 | Khairkhahan |
| 2004/0225354 A1 | 11/2004 | Allen et al. |
| 2004/0225355 A1 | 11/2004 | Stevens |
| 2005/0038509 A1 | 2/2005 | Ashe |
| 2005/0043790 A1 | 2/2005 | Seguin |
| 2005/0070999 A1 | 3/2005 | Spence |
| 2005/0075719 A1 | 4/2005 | Bergheim |
| 2005/0075727 A1 | 4/2005 | Wheatley |
| 2006/0020332 A1 | 1/2006 | Lashinski et al. |
| 2006/0020333 A1 | 1/2006 | Lashinski et al. |
| 2006/0025854 A1 | 2/2006 | Lashinski et al. |
| 2006/0025855 A1 | 2/2006 | Lashinski et al. |
| 2006/0206202 A1 | 9/2006 | Bonhoeffer et al. |
| 2006/0241745 A1 | 10/2006 | Solem |
| 2006/0287717 A1 | 12/2006 | Rowe et al. |
| 2007/0016286 A1 | 1/2007 | Herrmann et al. |
| 2007/0016288 A1 | 1/2007 | Gurskis et al. |
| 2007/0093890 A1 | 4/2007 | Eliasen et al. |
| 2007/0282429 A1 | 12/2007 | Hauser et al. |
| 2008/0243245 A1 | 10/2008 | Thambar et al. |
| 2009/0131880 A1 | 5/2009 | Speziali et al. |
| 2009/0248149 A1 | 10/2009 | Gabbay |

FOREIGN PATENT DOCUMENTS

| | | |
|---|---|---|
| EP | 1057460 A1 | 12/2000 |
| EP | 1356792 A1 | 10/2003 |
| EP | 1356793 A2 | 10/2003 |
| EP | 1472996 A1 | 11/2004 |
| WO | 9117720 A1 | 11/1991 |
| WO | 0112105 A1 | 2/2001 |
| WO | 0230335 A2 | 4/2002 |
| WO | 02085251 | 10/2002 |
| WO | 03003949 A2 | 1/2003 |
| WO | 03011195 A2 | 2/2003 |
| WO | 03028558 A2 | 4/2003 |

(56) References Cited

FOREIGN PATENT DOCUMENTS

| | | |
|---|---|---|
| WO | 03049648 A2 | 6/2003 |
| WO | 03088873 A1 | 10/2003 |
| WO | 2004014258 A1 | 2/2004 |
| WO | 2004019811 A2 | 3/2004 |
| WO | 2004023980 A2 | 3/2004 |
| WO | 2004082527 A2 | 9/2004 |
| WO | 2004093728 A2 | 11/2004 |
| WO | 2005009285 A2 | 2/2005 |
| WO | 2005020842 A2 | 3/2005 |
| WO | 2005062980 A2 | 7/2005 |
| WO | 2005087140 A1 | 9/2005 |
| WO | 2006054107 A2 | 5/2006 |
| WO | 2006111391 A1 | 10/2006 |
| WO | 2006127756 A2 | 11/2006 |
| WO | 2007100410 A2 | 9/2007 |
| WO | 2007130537 A1 | 11/2007 |
| WO | 2007149933 A2 | 12/2007 |
| WO | 2008100599 A1 | 8/2008 |
| WO | 2008100600 A1 | 8/2008 |
| WO | 2009045331 A1 | 4/2009 |
| WO | 2009052180 A1 | 4/2009 |
| WO | 2009052188 A1 | 4/2009 |
| WO | 2010057262 A1 | 5/2010 |
| WO | 2011002105 A1 | 1/2011 |

OTHER PUBLICATIONS

Khambadkone & Bonhoeffer, "Percutaneous implantation of atrio-ventricular valves; concept and early animal experience," Eurointervention Supplements (2006) 1 (Supplement A A24-A25) 2006.

HEART VALVE PROSTHESIS AND METHOD

CROSS REFERENCE TO RELATED APPLICATIONS

This application claims priority to U.S. patent application Ser. No. 13/130,180, filed Jan. 16, 2012, which is a national stage filing of PCT Patent Application Serial No. PCT/AU2009/001513, filed Nov. 20, 2009, which claims the benefit of priority to Australian Provisional Patent Application No. 2008906045, filed Nov. 21, 2008, and Australian Provisional Patent Application No. 2009900460, filed Feb. 9, 2009, all of which are incorporated herein by reference.

TECHNICAL FIELD

The present invention relates to a heart valve prosthesis and associated method of treating a failed or failing heart valve. The invention is particularly related to a two-component heart valve prosthesis that is implantable by a two-step approach.

BACKGROUND OF THE INVENTION

Heart valve regurgitation is a condition whereby the heart valve does not seal completely as a result of disease or injury, and may have fatal consequences. Valve stenosis is a condition where the valve is narrowed and cannot open normally. Whilst valve stenosis can be treated by valvuloplasty (by balloon dilatation), this often results in the valve leaking and may require valve replacement. Aortic valvuloplasty is generally not a very effective or durable treatment for aortic stenosis.

Malfunctioning heart valves have typically been replaced with mechanical or biologic heart valve prostheses using highly invasive open-heart surgical techniques. Surgical mitral valve replacement is quite invasive and cannot be performed on many sick patients with severe mitral regurgitation. This procedure often results in resection of the anterior leaflet of the mitral valve which could lead to further left ventricular dysfunction. Whilst there has been some success in developing replacement stent based aortic valve prostheses for delivery via percutaneous catheter-based methods, these techniques have not been particularly successful when applied to mitral valve prostheses.

Mitral valve replacement is firstly made difficult as a result of the anatomy of the mitral valve, and particularly that of the mitral valve annulus in which the mitral valve leaflets are located. The mitral valve annulus is typically very distorted, and of unpredictable and non-uniform geometries, as compared to the relatively uniform aortic valve annulus. This unpredictable anatomy makes it difficult to design a pre-constructed mitral valve prosthesis that would fit the mitral valve annulus in a satisfactory manner for safe, stable and meticulous deployment.

Further, unlike the aortic valve annulus which is entirely surrounded by muscular tissue, the mitral valve annulus is bounded by muscular tissue on the outer wall only, with the inner side of the mitral valve annulus being bounded by a thin vessel wall which separates the mitral valve annulus and the aortic outflow tract. As a result, the mitral valve annulus cannot be subjected to any significant radial forces, as would be typical with an expanding stent type of valve prosthesis, as such radial forces would tend to collapse the aortic outflow tract, resulting in circulatory collapse with likely fatal consequences. As such, stent type valve prostheses are presently generally not suitable for use as a replacement mitral valve.

Mitral valve replacement techniques have also generally advocated removal of the native valve prior to location of the replacement mitral valve prosthesis. This is a technically extremely challenging task associated with the potentially fatal complication of profound mitral regurgitation that may not be adequately addressed by the subsequent valve replacement. The lack of an effective mitral valve may lead to overwhelming hemodynamic instability that may not be tolerated by the already compromised left ventricle and overwhelming pulmonary oedema may rapidly result.

Known stent based aortic valves are also not generally repositionable and therefore precise placement is difficult. This could result in important structures such as the coronary arteries being compromised as a result. Moreover, post-stenotic dilatation of the aorta may result in imprecise apposition of current stent based aortic valves, resulting in significant paravalvular leaks. For the same reason, current stent based aortic valves are typically not recommended for the treatment of pure aortic regurgitation. Current stent based aortic valves are also typically subject to fatigue and resultant fracture.

Further, various previously proposed replacement heart valve prostheses are relatively bulky and are thus not suited for percutaneous delivery using small diameter catheters, with more invasive larger catheters being required.

OBJECT OF THE INVENTION

It is the object of the present invention to substantially overcome or at least ameliorate at least one of the above disadvantages.

SUMMARY OF THE INVENTION

In a first aspect, the present invention provides a heart valve prosthesis comprising a housing component and a valve component;

wherein said housing component comprises a housing body having a housing passage extending therethrough;

said housing body being configured to be located in, or adjacent to and communicating with, a native valve orifice of a heart;

said housing component being configurable between a housing collapsed state for delivery to the native valve orifice via catheter and a housing expanded state to engage structure of the heart to fix said housing body in relation to the native valve orifice;

further wherein said valve component comprises:

a valve body having a valve passage extending therethrough;

said valve body being configured to be located at least partially within said housing passage with said valve passage extending along said housing passage; and one or more flexible valve elements secured to said valve body and extending across said valve passage for blocking blood flow in a first direction through said valve passage whilst allowing blood flow in an opposing second direction through said valve passage;

said valve component being configurable between a valve collapsed state for delivery to said housing passage via catheter, when said housing body is in said housing expanded state following delivery to the native valve orifice, and an expanded state to engage said housing component and/or structure of said heart to fix said valve body at least partially within said housing passage.

The valve body is typically configured to be located and fixed wholly within the housing passage.

In various embodiments, the housing body comprises a housing body frame formed of one or more elongate elastic housing body frame elements. The housing body may further comprise a flexible housing wall fixed to the housing body frame and extending about the housing passage.

In some embodiments, the housing body is substantially cylindrical, whilst in other embodiments the housing body is tapered.

In various preferred embodiments, the housing passage is double-tapered, defining a housing passage neck portion located between opposing ends of the housing passage. In such embodiments the valve body is typically also double-tapered, defining a valve body neck portion adapted to co-operate with the housing passage neck portion to secure the valve body within the housing passage.

The valve body may comprise a valve body frame formed of one or more elongate elastic valve body frame elements.

The valve component may comprise a stent valve, the valve body being configured to be fixed at least partially within the housing passage by expansion of the valve body.

The housing component may further comprise one or more flexible temporary valve elements secured to the housing body and extending across the housing passage for inhibiting blood flow in a first direction through the housing passage whilst allowing blood flow in an opposing second direction through the housing passage prior to delivery of the valve component.

In various embodiments, the prosthesis is an atrioventricular valve prosthesis for replacing an atrioventricular valve (that is, a mitral valve or tricuspid valve). In particular, the prosthesis may be a mitral valve prosthesis for replacing a mitral valve.

In certain embodiments, the housing component further comprises a skirt extending about a periphery of the housing body for inhibiting blood flow in the first direction between the housing body and a wall of the native valve orifice.

The housing body may be configured to be located with an end of the housing adjacent to and communicating with the native valve orifice and the skirt is located adjacent to the end of the housing body.

For atrioventricular valve applications, the housing component preferably includes an anchoring mechanism secured to the housing body and configured to engage native tissue of the heart. Typically, the anchoring mechanism is configured to engage native tissue of the heart outside of the native valve orifice.

The anchoring mechanism may be configured to engage a wall of a ventricle of the heart communicating with the native valve orifice. Alternatively or additionally, the anchoring mechanism is configured to engage a wall of an atrium of the heart communicating with the native valve orifice.

In certain embodiments, the anchoring mechanism includes a plurality of primary prongs secured to and spaced about the housing body. The primary prongs are typically configured to engage native tissue of the heart outside of the native valve orifice.

The primary prongs may each be secured to the housing body by one or more legs extending from an end of the housing body.

The legs typically extend into a ventricle of the heart communicating with the valve orifice, the primary prongs being configured to engage a wall of the ventricle and/or sub-valvular tissue, such as papillary tissue or the chordae tendineae, of the heart.

The anchoring mechanism may further comprise a plurality of secondary prongs secured to and spaced about the housing body. The secondary prongs may be located such that, in use, the secondary prongs are located on an opposing side of the native valve orifice to the primary prongs.

In one embodiment, the valve component includes a collapsible anchor device for anchoring the valve body to a septum of the heart and a flexible anchor line extending between the valve body and the anchor device, the anchor device being collapsible for delivery via catheter with the valve body.

In one or more embodiments, the prosthesis is a semilunar valve prosthesis for replacing a semilunar valve (that is, an aortic valve or pulmonary valve). In particular, the prosthesis may be an aortic valve prosthesis for replacing an aortic valve.

For semilunar valve applications, the housing component is typically configured to engage a wall of the native valve orifice to fix the housing body in relation to the native valve orifice.

The housing component may comprise a generally tubular housing body formed of an elastically compressible material. The housing body may be integrally formed of a polymeric material.

In a second aspect, the present invention provides a method of replacing a failing or failed heart valve of a patient, said method comprising the steps of:

a) delivering a housing component of a heart valve prosthesis into, or adjacent to and in communication with, the native valve orifice of the heart valve to be replaced;

b) securing said housing component to structure of the heart so as to fix said housing component in relation to the native valve orifice;

c) delivering a valve component of said heart valve prosthesis at least partially into a housing passage defined by said housing component; and d) securing said valve component at least partially into said housing passage.

Typically, the valve component is delivered and secured wholly within the housing passage.

Typically, the housing component is delivered via catheter in a collapsed state and expanded into an expanded state within, or adjacent to and in communication with, the native valve orifice, thereby engaging structure of the heart to fix said housing component in relation to the native valve orifice. The valve component is delivered via catheter in a collapsed state and expanded into an expanded state within the housing passage, thereby engaging the housing body and/or structure of the heart to fix the valve body within the housing passage.

The housing component may be secured to structure of the heart outside of the native valve orifice.

The heart valve may be an atrioventricular valve, typically a mitral valve.

For a mitral valve application, the method may further comprise the step of creating a septal puncture in the inter-atrial septum of the heart, the housing component and the valve component each being delivered percutaneously via catheter through the venous system of the patient and through the septal puncture.

Alternatively, the method may further comprise the step of creating an apex puncture in the apex of the left ventricle of the heart, the housing component and the valve component each being delivered via catheter through the apex puncture.

The heart valve may be a semilunar valve, typically an aortic valve.

For an aortic valve application, the housing component and the valve component may each be delivered percutaneously via catheter through the arterial system of the patient.

BRIEF DESCRIPTION OF THE DRAWINGS

Preferred embodiments of the present invention will now be described, by way of examples only, with reference to the accompanying drawings wherein.

DETAILED DESCRIPTION OF THE PREFERRED EMBODIMENTS

Figure 1:
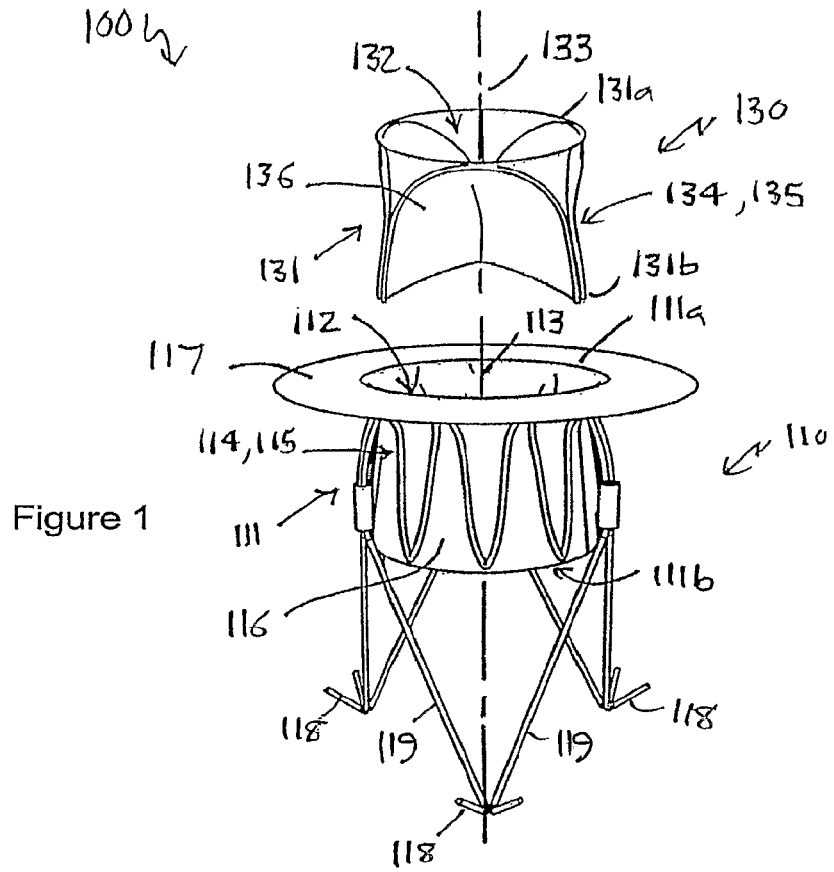
FIG. 1 is a perspective view of a heart valve prosthesis according to a first embodiment in a disassembled state.

Referring to FIGS. 1 to 4 of the accompanying drawings, a first embodiment of a heart valve prosthesis 100 is a two-component assembly, comprising a housing component 110 and a valve component 130. The heart valve prosthesis 100 is described here in terms of a mitral valve prosthesis for replacing a failed or failing mitral valve, however the heart valve prosthesis is also applicable to other heart valves including, in particular, the tricuspid valve.

The housing component 110 includes a housing body 111 that has a housing body first end 111a, a housing body second end 111b, and a housing passage 112 extending between the housing body first and second ends 111a, 111b along a longitudinal housing axis 113. As will be discussed further below, the housing body 111 is configured to be located adjacent to and communicating with the native mitral valve orifice of the heart with the housing body second end 111b located within the left ventricle and the housing body first end 111a located adjacent to and communicating with the mitral valve orifice, still located on the left ventricular side of the mitral valve orifice, but adjacent the left atrium. In other embodiments discussed below, the housing body is configured to be located in the native mitral valve orifice with the housing body first end located in the left atrium with the housing body extending through the mitral valve orifice. In still other embodiments, the housing body may be configured to be located on the left atrial side, adjacent to the native mitral valve orifice. Accordingly, the first end will hereinafter be referred to as the atrial end and the second end referred to as the ventricular end, although alternate terminology would be appropriate for applications in replacement of heart valves other than the mitral valve.

The housing body 111 is here formed of a generally annular housing body frame 114 formed of a single elongate elastic housing body frame element 115 configured in a sinusoidal or concertina type configuration extending annularly about the housing passage 112. Rather than being formed as a single element, the housing body frame 114 could be formed of several elements joined together by welding, clips or other suitable means. The housing body frame element 115 is typically in the form of a wire formed of a super elastic shape memory material. A particularly suitable material is nitinol, a nickel-titanium alloy that is known for use in catheter delivered prosthesis applications. Other suitable elastic metallic materials include stainless steel, other titanium alloys and cobalt chromium molybdenum. Other suitable relatively rigid yet elastic metal alloys or non-metallic materials may be utilized as desired. The wire forming the housing body frame 115 will typically have a diameter of the order of 0.3 mm to 0.4 mm, however wire of alternate diameters is also envisaged. Rather than being formed of wire, the housing body frame 114 could be cut from a cylindrical tube of material, typically a super elastic shape memory alloy such as nitinol. The tube could be cut by laser to provide a largely open unitary frame structure which could be subsequently heat shaped to tailor the cross-section of the housing body along its length.

The housing body 111 also has a flexible housing wall 116 that is fixed to the housing body frame 114 and extends about the housing passage 112. The housing wall 116 may be formed of a suitable flexible biological material, such as pericardial material. Alternatively, the housing wall 116 may be formed of any suitable flexible non-biological material, such as, for example, silicone, polyester or dacron. The housing wall 116 will typically be fixed to the housing body frame 114 by suturing. The housing wall 116 serves to enclose the housing passage 112, inhibiting leakage through the housing body frame 114.

The housing component 110 further preferably includes a flexible skirt 117 extending about a periphery of the housing body 111 for inhibiting blood flow in a first direction from the left ventricle into the left atrium.

For configurations where the housing body 111 is intended to be located adjacent to the native mitral valve orifice on the ventricular side, rather than within the orifice, the flexible skirt 117 is located at the housing body atrial (i.e., first) end 111a such that, in use, it will engage and seal with tissue surrounding the valve orifice on the ventricular side, as will be discussed below.

In configurations where the housing body 111 is intended to be located on the atrial side of the native mitral valve orifice, the flexible skirt will generally be located at the housing body ventricular (i.e., second) end 111b such that, in use, it will engage and seal with tissue surrounding the valve orifice on the atrial side. For configurations where the housing body is intended to extend through the native mitral valve orifice, the flexible skirt may be located on either side of the native valve orifice in use.

The flexible skirt 117 will typically be formed of the same material as the housing wall 116. The flexible skirt 117 and housing wall 116 will also typically be sutured to one another. It is also envisaged that the flexible skirt may be reinforced with wire or any of various other forms of reinforcement so as to provide the skirt with some degree of stiffness.

The housing component 110 also includes an anchoring mechanism secured to the housing body 111. Here the anchoring mechanism includes a plurality of primary prongs 118 secured to and spaced about the housing body 111. The primary prongs 118 are here each secured to the housing body 111 by one or more legs 119 extending from the housing body ventricular (i.e. second) end. The primary prongs 118 are thus hereinafter described as ventricular prongs 118. The ventricular prongs 118 are here arranged in two sets of three individual prongs 118 formed by bending the ends of each of the legs 119 so as to project radially outwardly and longitudinally back toward the housing body 111. The ventricular prongs 118 are thus configured to engage native tissue structure of the heart outside of the native valve orifice, rather than relying on fixation to the delicate, thin tissue constituting the mitral valve orifice wall. In the particular arrangement depicted, the legs 119 longitudinally offset the ventricular prongs 118 from the housing body 111 such that, in use, the ventricular prongs engage the wall of the left ventricle and/or subvalvular tissue, such as papillary muscle tissue or the chordae tendineae, as will be discussed below. The ventricular prongs 118 and legs 119 are formed of a super elastic shape memory material in wire form, typically the same as the housing body frame element 115.

It is envisaged, however, that the prongs might be configured to engage the mitral valve orifice wall. Whilst the mitral valve orifice wall is generally not capable of sustaining any significant radial forces as might be applied by a stent, it generally will be capable of sustaining point anchor loads as may be applied by the prongs. The ventricular prongs 118 may be in the form of hooks or barbs. In place of the prongs, the anchoring mechanism may be in any of various alternate forms including clips, clamps, staples or adhesives. For embodiments configured to replace other heart valves, particularly the aortic valve or pulmonary valve, it is envisaged that the housing body might be in a radially expandable stent form that directly engages the native orifice wall to fix the housing component in relation to the valve orifice.

Figure 2:
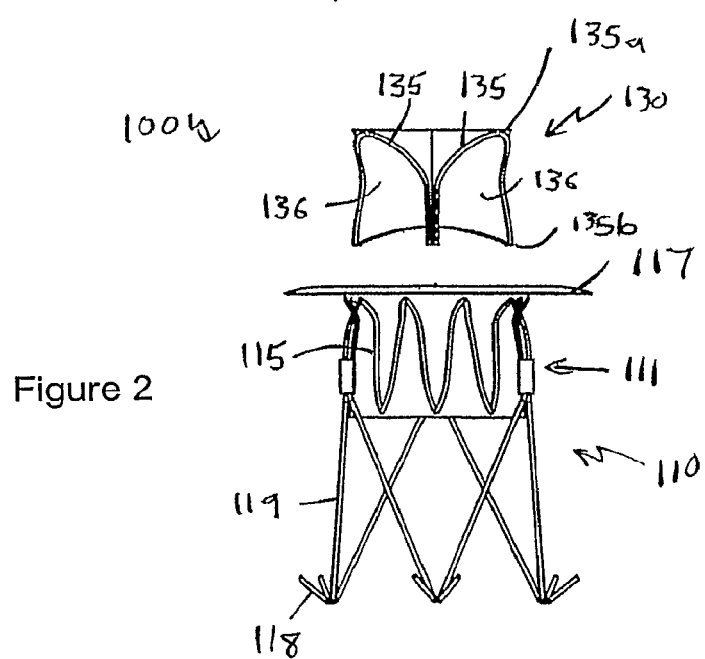
FIG. 2 is a front elevation view of the heart valve prosthesis of FIG. 1 in the disassembled state.

The entire housing component 110 is elastically collapsible from a stable expanded state, as depicted in FIGS. 1 and 2, into an unstable collapsed state extending along the housing longitudinal axis 113 to allow delivery of the housing component 110, typically percutaneously, by catheter.

The entire surface of the housing component 110 would typically be coated with a suitable coating to inhibit, or at least reduce the effect of, thrombus formation. Particularly suitable coatings for application to the housing body frame 114 include polyester coatings, textured metallic coatings, heparin based coatings, diamond-like carbon coatings, parylene coatings and fluoropolymer coatings such as polytetrafluoroethylene. Textured metallic coatings may be applied in the form of sintered nitinol or titanium and serve to add texture to the surface, helping to ensure any thrombus formed does not break free into the bloodstream. Such textured surfaces also promote tissue ingrowth to the foreign housing body frame 114. The same coating may be applied to the ventricular prongs 118 and legs 119. Coatings that would be particularly suitable for application to the housing wall 116 and flexible skirt 117 to inhibit thrombus formation include heparin based coatings, parylene coatings and fluoropolymer based coatings such as polytetrafluoroethylene.

The valve component 130 includes a valve body 131 that has a valve body atrial (i.e., first) end 131a, a valve body ventricular (i.e., second) end 131b and a valve passage 132 extending between the valve body atrial and ventricular ends 131a, 131b along a longitudinal valve axis 133. In the arrangement depicted, the valve body 131 is formed of a valve body frame 134 formed of three elongate elastic valve body frame elements 135. Each of the valve body frame elements 135 is in the general form of an arch formed of a wire of super elastic shape memory material, typically the same as that of the housing body frame element 115. Each valve body frame element 135 has its opposing ends 135b located at the valve body ventricular end 131b and its vertex 135a located at the valve body atrial end 131a. The ends 135b of each valve body frame element are secured to each other, typically by welding or crimping, however other suitable metals are also envisaged. It is also envisaged that the valve body frame could be formed of a single valve body frame element, such that only the opposing ends of the single valve body frame element would be sewed to each other.

A flexible valve element 136 is secured to each of the valve body frame elements 135, typically by suturing. The valve elements 136 may be formed of a suitable flexible biological material, such as pericardial material including bovine pericardium or kangaroo pericardium. The valve elements 136 may alternatively be formed of a suitable flexible non-biological material. The valve elements 136 are secured to the valve body frame elements 135 and configured such that they extend across the valve passage 132 in a manner that they block blood flow in a first direction through the valve passage 132 from the valve body ventricular end 131b toward the valve body atrial end 131a, whilst allowing blood flow in an opposing second direction. The valve elements 136 each extend laterally beyond their respective valve body frame element 135 toward the valve body atrial end 131a, with adjacent valve elements 136 overlapping or being sutured to form a continuous valve leaflet structure about the circumference of the valve body 131 at the valve body atrial end 131a.

The entire valve component 130 is elastically collapsible from a stable elastically expanded state, as depicted in FIGS. 1 and 2, into an unstable collapsed state extending along the valve longitudinal axis 133 to allow delivery of the valve component 130, typically percutaneously, by catheter.

Forming the heart valve prosthesis 100 as two separate percutaneously deliverable components allows for use of a smaller catheter than would otherwise be possible if the housing and valve were formed as a single component. Forming the heart valve prosthesis as two separate components also enables provision of a relatively simple (and thereby inexpensive) valve component which can be discarded if biological material forming the valve elements has reached its shelf life, whilst retaining the housing component, which might employ non-biological material for the flexible housing wall 116 and flexible skirt 117, thereby providing it with a longer shelf life. The two component prosthesis also enables utilization of commonly known stent based aortic valves as the valve component for a mitral valve prosthesis. Handling and preservation of the simpler valve component 130 and securing of the valve elements to the valve body by the bedside may also be simplified. Further, the two component prosthesis potentially allows for the placement of the prosthesis in different locations of the heart, including different sized heart valve orifices, by altering the size or configuration of the housing component only, using a common valve component.

Figure 3:
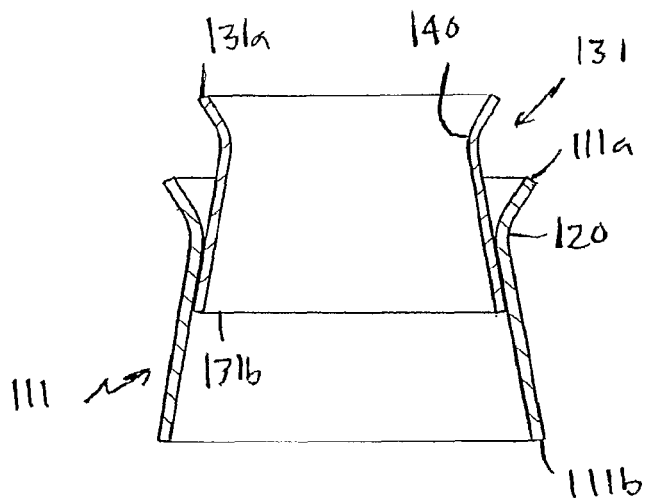
FIG. 3 is a schematic representation of the housing body and valve body of the heart valve prosthesis of FIG. 1 in a partly assembled state.
Figure 4:
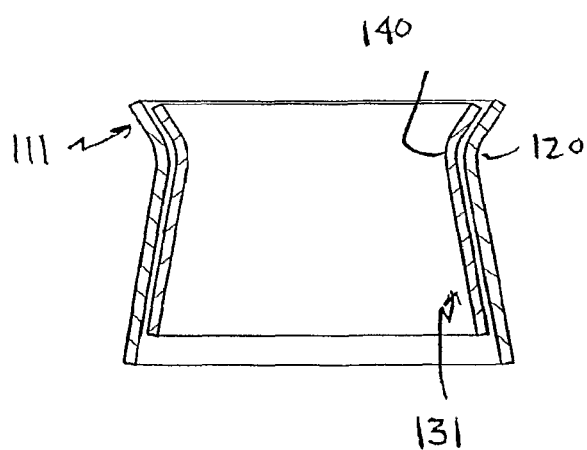
FIG. 4 is a schematic representation of the housing body and valve body of FIG. 3 in an assembled state.

With particular reference to FIGS. 3 and 4, both the housing body 111 and the valve body 131 are double-tapered providing an asymmetric hourglass-type shape. The double-tapered shape of the housing body 111 provides a double-tapered housing passage 112. The housing passage 112 has a reduced neck portion 120 located between the housing body atrial end 111a and housing body ventricular end 111b. The valve body 131 also has a neck portion 140 located between the valve body atrial end 131a and valve body ventricular end 131b. The housing passage 112 and valve body 131 are sized such that the double-taper acts to secure the valve body 131 within the housing passage 112, with the valve passage neck portion 140 co-operating with the housing body neck portion 120. Alternatively, the housing passage 112 and valve body 131 could be substantially cylindrical or singularly tapered, and be provided with alternate means for securing the valve body 131 within the housing body 111, such as connectors, prongs or other suitable fastening means.

Replacement of a failed or failing mitral valve by implantation of the mitral valve prosthesis 100 of the first embodiment described above using a percutaneous venous approach will now be described with reference to FIGS. 5 through 11. The venous system of the patient to be treated is firstly accessed by a puncture, typically in the groin area, accessing the femoral vein. Access to the venous system might alternatively be made via other large peripheral veins such as the sub-clavian or jugular veins. The femoral vein is, however, preferred given the compressibility of the femoral vein once a catheter is removed from the patient to achieve hemostasis.

Figure 5:
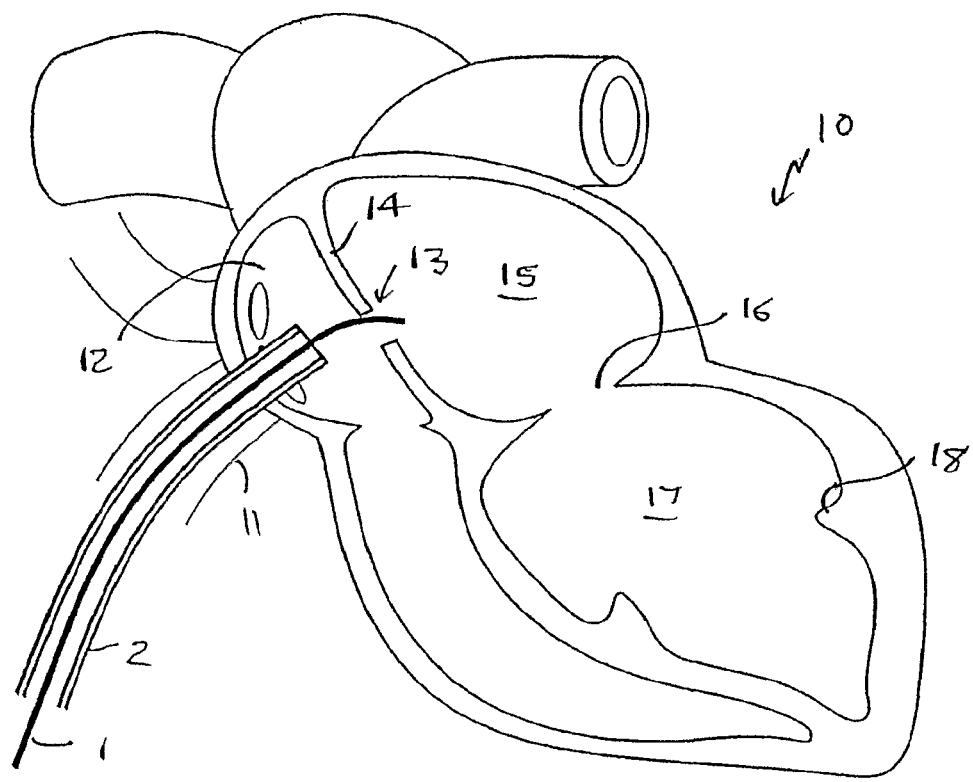
FIG. 5 is a schematic cross-sectional front elevation view of a heart depicting a catheter and guide wire advanced into the right atrium with a puncture formed in the inter-atrial septum.

Referring to FIG. 5, a guide wire 1, typically having a diameter of approximately 0.85 mm to 1.7 mm, is inserted through the puncture and along the femoral vein and via the inferior vena cava 11 to the right atrium 12 of the patient's heart 10. If additional steadying of the guide wire 1 is desired, a snare may be introduced to the heart 10 through an arterial approach from the left or right femoral artery, aorta and aortic valve. The snare will then engage a J-tip on the end of the guide wire 1 and draw the end of the guide wire 1 through the arterial system to the exterior of the patient so that opposing ends of the guide wire 1 may be steadied.

A catheter 2, typically having a diameter of about 20 to 24 French (6.7 mm to 8.0 mm) is then advanced over the guide wire 1 and into the right atrium 12. A puncture 13 is then made in the inter-atrial septum 14 using conventional equipment advanced by the catheter 2 in a known manner. The guide wire 1 and catheter 2 are then further advanced through the septal puncture 13 and into the left atrium 15.

Figure 6:
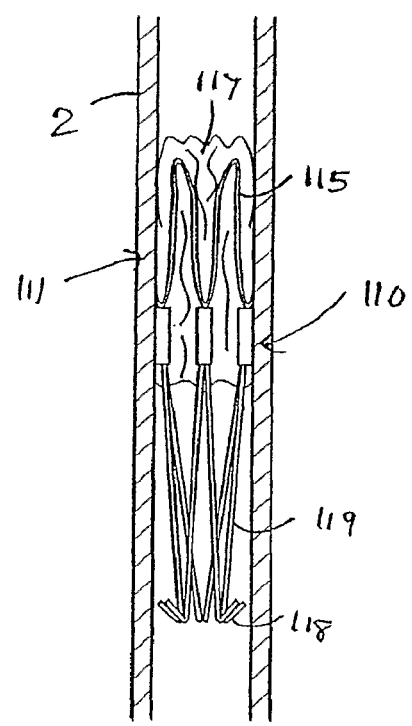
FIG. 6 is a cross-sectional fragmentary view of a catheter with the housing component of the heart valve prosthesis of FIG. 1 loaded therein.
Figure 7:
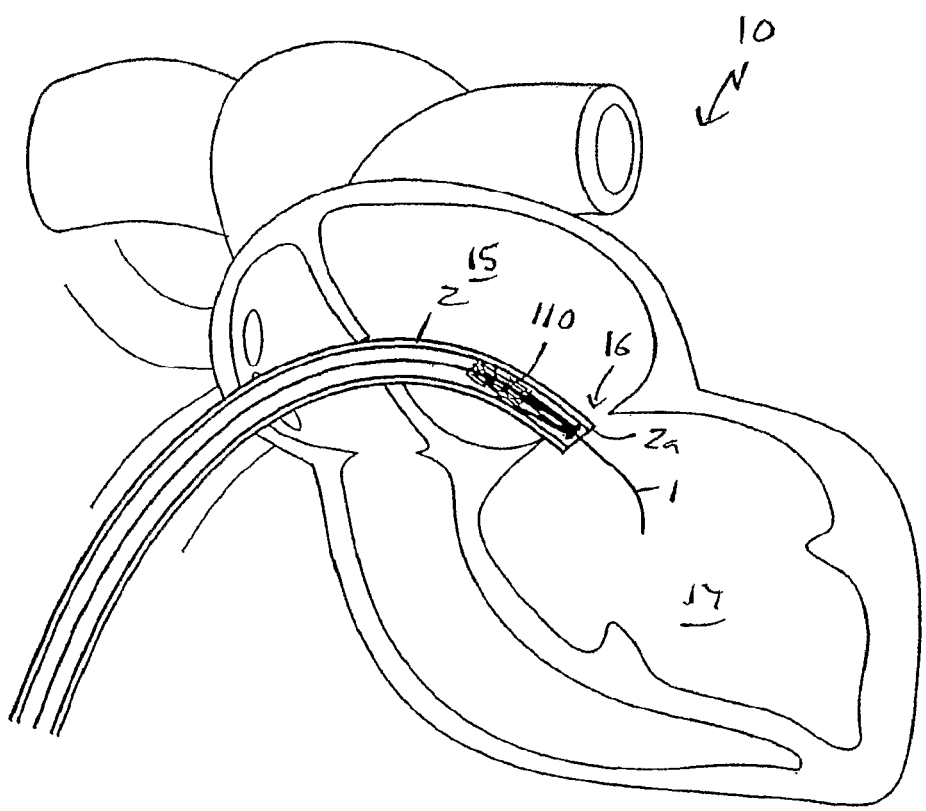
FIG. 7 is a schematic cross-sectional front elevation view of the heart of FIG. 5 with the housing component advanced to the end of the catheter.
Figure 8:
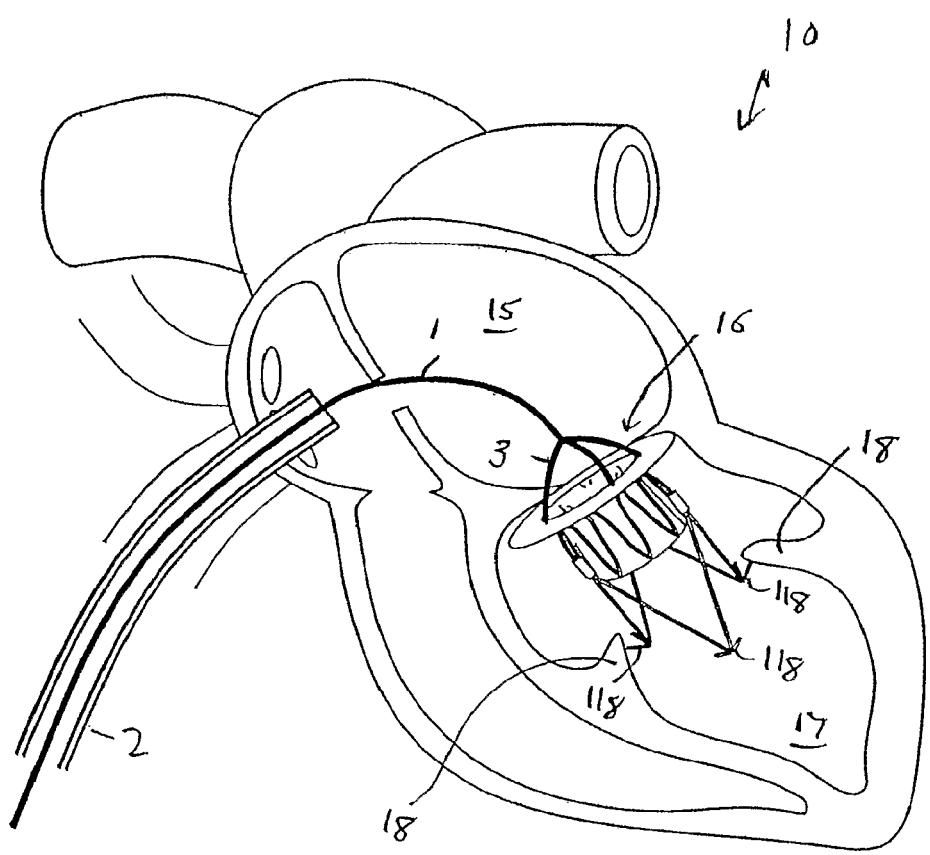
FIG. 8 is a schematic cross-sectional front elevation view of the heart of FIG. 5 with the housing in the expanded state adjacent the mitral valve orifice.

Referring to FIG. 6, the housing component 110 of the mitral valve prosthesis 100 is collapsed and fed into the catheter 2 with the housing body atrial end 111a trailing the housing body ventricular end 111b. The housing component 110 is then delivered percutaneously by first being advanced along the guide wire 1 to the leading end 2a of the catheter as depicted in FIG. 7. The leading end 2a of the catheter 2 extends through the native mitral valve orifice 16 and into the left ventricle 17, carefully positioning the housing component 110 (that remains collapsed inside the catheter 2) in the left ventricle 17 adjacent the mitral valve orifice 16. The failed or failing native mitral valve leaflets will typically be left in place. The catheter 2 is then withdrawn whilst leaving the guide wire 1 and housing component 110 in place, such that the housing component 110 is allowed to expand into the left ventricle 17, as depicted in FIG. 8. The ventricular prongs 118 engage the papillary muscles 18 within the left ventricle 17 and/or the wall of the left ventricle 17, thereby securing the housing body 111 in relation to the mitral valve orifice 16. The ventricular prongs 118 may alternatively or additionally engage other subvalvular tissue of the heart, particularly the chordae tendineae. The ventricular prongs 118 and legs 119 may also assist in preventing complete collapse of the left ventricle, where opposing walls make contact in what is termed "obliteration", as the ventricular prongs 118 will act to prop the left ventricle 17 open to some extent in a stent-like manner. This may be beneficial to patients suffering diastolic heart failure. To achieve this effect, the legs 119 should be of sufficient structural stiffness to provide the desired supporting effect.

Figure 9:
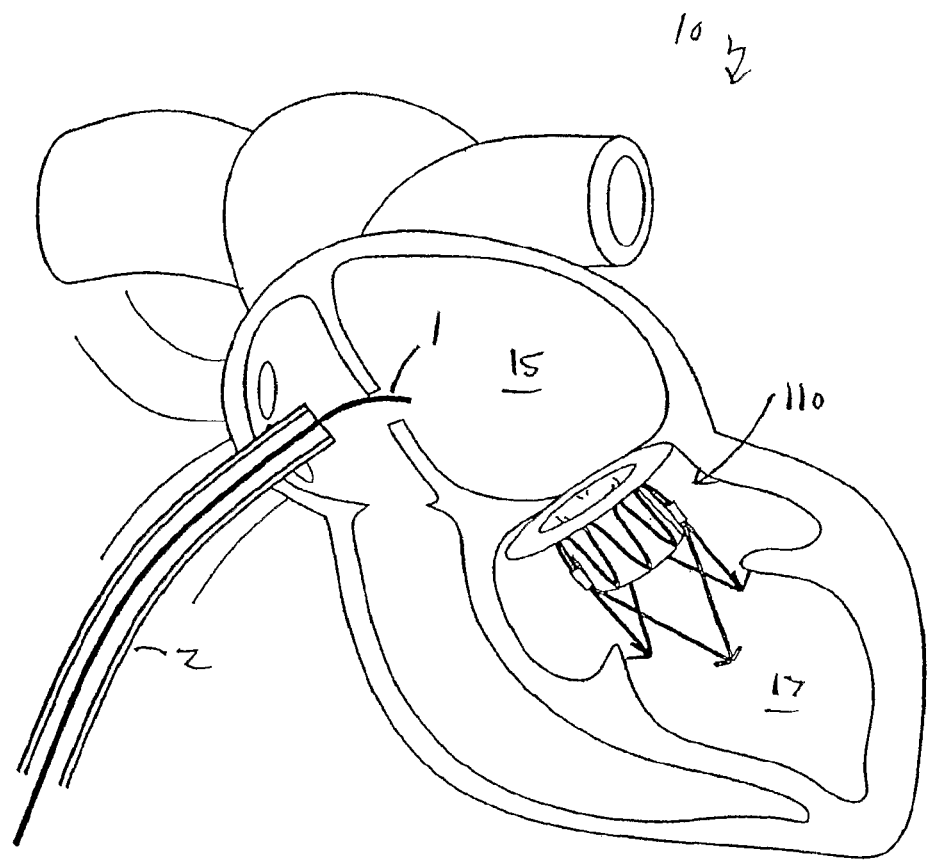
FIG. 9 is a schematic cross-sectional front elevation view of the heart of FIG. 5 with the guide wire withdrawn from the housing component.

At this stage, the housing component 110 remains attached to the guide wire 1 by way of a tether 3 that allows for some re-positioning of the housing body 111 in relation to the mitral valve orifice 16 and, if greater adjustment is required, allows the catheter 2 to be advanced back over the housing component 110, re-collapsing the housing component 110 into the catheter 2, for further re-positioning as required. Once the housing component 110 is in the correct position, the tether 3 is detached from the housing component 110 and the guide wire 1 withdrawn back into the catheter 2, as depicted in FIG. 9.

Figure 10:
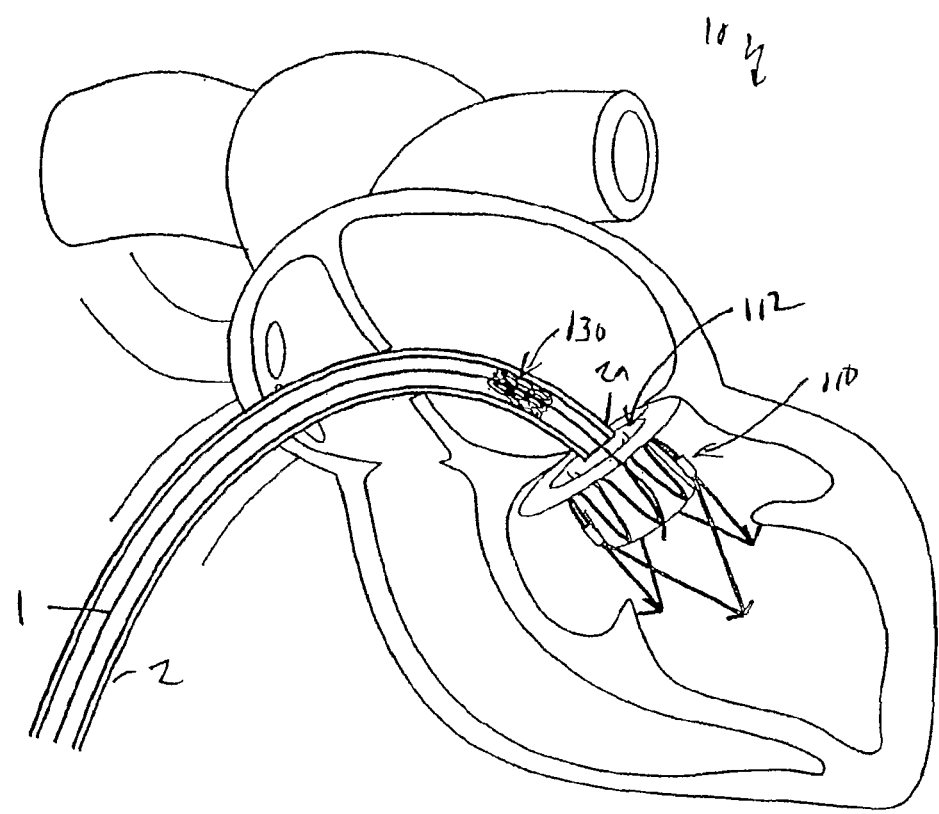
FIG. 10 is a schematic cross-sectional front elevation view of the heart of FIG. 5 with the valve component of the heart valve prosthesis of FIG. 1 advanced toward the end of the catheter.

Referring to FIG. 10, the valve component 130 of the heart valve prosthesis 100 is next collapsed and loaded into the catheter 2, with the valve body atrial end 131a trailing the valve body ventricular end 131b.

Figure 11:
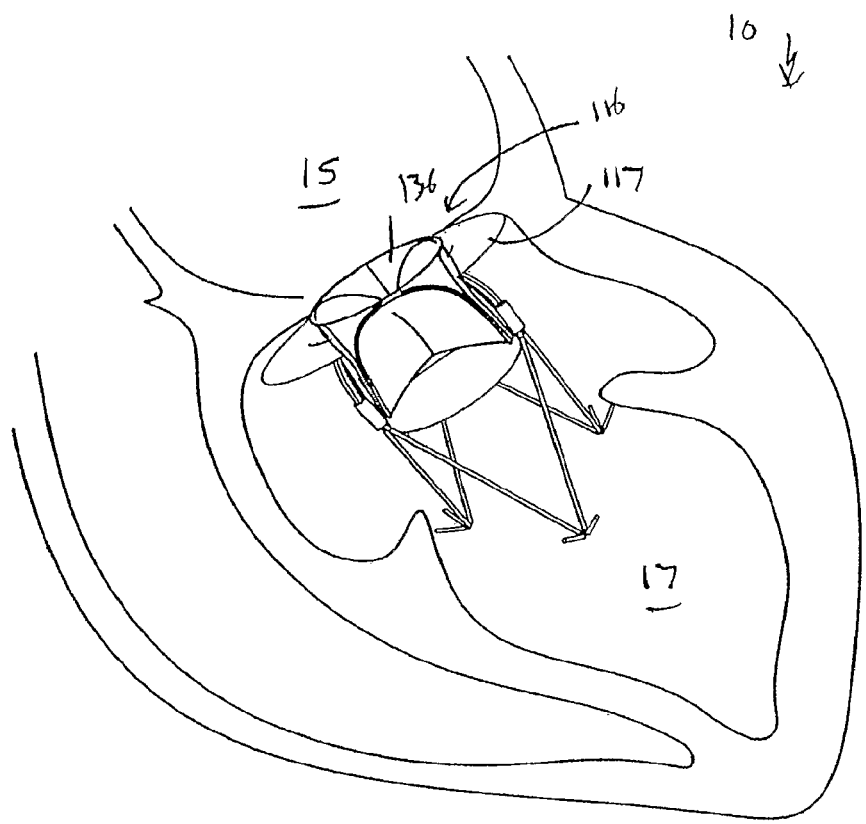
FIG. 11 is a cross-sectional front elevation view of the heart of FIG. 5 with the heart valve prosthesis of FIG. 1 fully implanted.

The valve component 130 is advanced along the guide wire 1 toward the second end 2a of the catheter which itself is advanced to the atrial end of the housing passage 112 within the housing component 110, ready for deployment of the valve component 130. Once the collapsed valve component 130 is located in the appropriate position within the housing passage 112, the catheter 2 is withdrawn, allowing the valve component 130 to elastically expand into engagement with the housing body frame 114 of the housing body 111, securing the valve component 130 to the housing body 111 with the valve passage 132 extending along the housing passage 112. The catheter 2 and guide wire 1 are then withdrawn from the patient, leaving the assembled heart valve prosthesis 100 in position as depicted in FIG. 11 effectively replacing the native mitral valve. The (ineffective) native mitral valve would typically be left in place, with the native valve leaflets retained on the outside of the housing component 110 where they may assist in preventing paravalvular leakage during ventricular systole. Blood flow from the left atrium into the left ventricle during atrial systole is provided for through the valve elements 136, whilst the same valve elements 136 prevent back flow from the left ventricle 17 into the left atrium 15 during ventricular systole. Back flow from the left ventricle 17 into the left atrium 15 from outside of the housing component 110 is also inhibited by virtue of the flexible skirt 117 which effectively seals against the periphery of the mitral valve orifice 16 against any back flow when the left ventricle 17 contracts and pressurizes during ventricular systole.

The entire procedure may be performed under the guidance of fluoroscopy transthoracic and transesophageal echocardiography in a known manner.

In a modification of the procedure described above, a larger first catheter (typically about 24 French) is first advanced over the guide wire 1 to a position extending through the native mitral valve orifice 16, displacing the native mitral valve leaflets. A smaller catheter 2 (typically 20-21 French) is then advanced through the first catheter, delivering the housing component 110. Once the second catheter 2 is in position ready for release of the housing component 120, the first catheter is withdrawn slightly, allowing the housing component 110 to be expanded into position. The valve component 130 is then delivered either through the same second catheter 2 or another catheter, again advancing through the first catheter.

Replacement of a failed or failing mitral valve by implantation of the mitral valve prosthesis 100 of the first embodiment using an alternate trans-apical approach will now be described with reference to FIGS. 12 through 17. This method provides more direct access to the left ventricle 17 of the patient's heart 10 via the apex 19 of the left ventricle 17. Access to the apex 19 of the left ventricle 17 may be provided either surgically or percutaneously. In a surgical procedure, a limited surgical incision may be first made in the precordial region of the thorax, providing direct and visual access to the exterior of the apex 19 of the left ventricle 17. Alternatively, for a percutaneous procedure, a needle puncture of the precordial region of the thorax may be made and the region is then dilated by way of a balloon catheter so as to provide access to the exterior of the apex 19 of the left ventricle 17.

Figure 12:
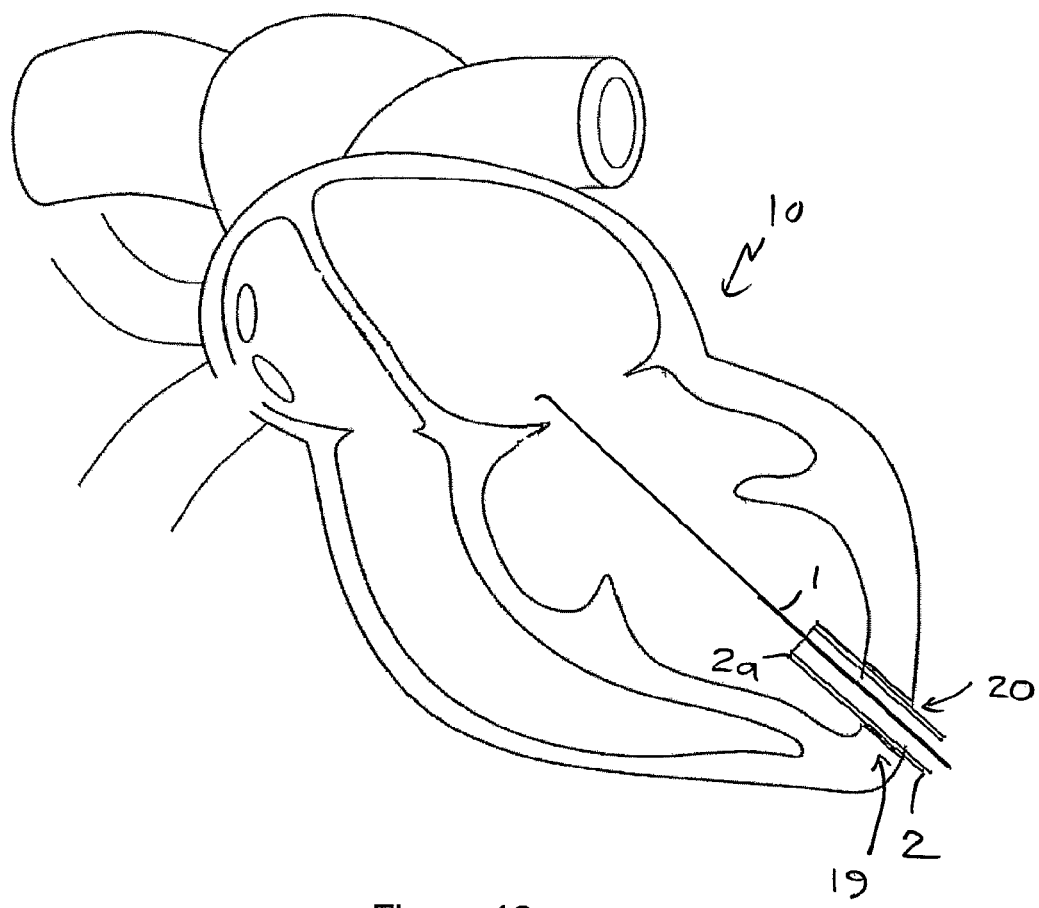
FIG. 12 is a schematic cross-sectional front elevation view of a heart depicting a catheter and guide wire advanced into the left ventricle through a puncture formed in the apex of the left ventricle.

Referring to FIG. 12, the left ventricle 17 is then accessed by creating a puncture 20 in the apex 19 of the left ventricle 17. For the surgical procedure, the puncture 20 may be created by way of direct surgical incision. For the percutaneous procedure, the puncture 20 may be created by way of conventional cutting equipment advanced by catheter. A guide wire 1, typically having a diameter of approximately 0.85 mm to 1.7 mm, is inserted directly through the puncture 20 in the surgical procedure or following balloon dilation of the area in the percutaneous procedure.

A catheter 2, typically having a diameter of about 20 to 24 F (6.7 mm to 8.0 mm) is then advanced over the guide wire 1 and into the left ventricle 17 through the puncture 20, as depicted in FIG. 12.

Figure 13:
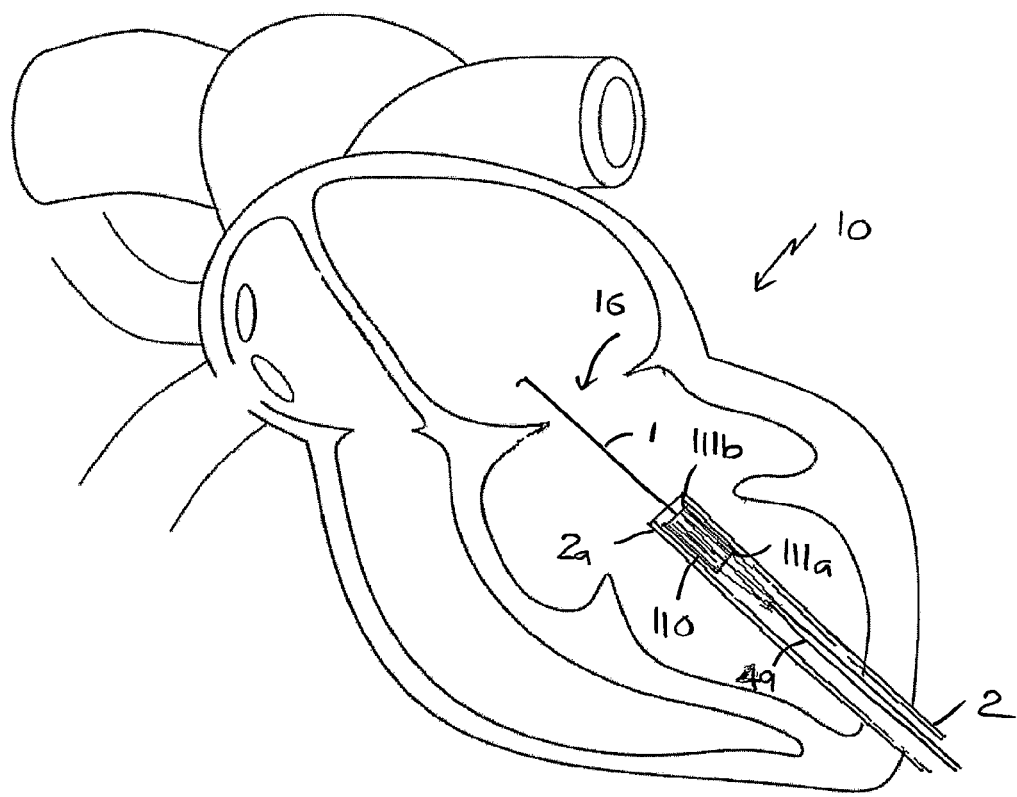
FIG. 13 is a schematic cross-sectional front elevation view of the heart of FIG. 12 with the housing component advanced to the end of the catheter.

Referring to FIG. 13, the housing component 110 of the mitral valve prosthesis 100 is collapsed and fed into the catheter 2 with the housing body ventricular end 111b trailing the housing body atrial end 111a. The housing component is delivered to the left ventricle 17 by being advanced along the guide wire 1 to the leading end 2a of the catheter 2. The leading end 2a of the catheter 2 is carefully positioned within the left ventricle 17 adjacent the mitral valve orifice 16, ready for deployment of the housing component 110. The failed or failing native mitral valve leaflets would typically be left in place and may be displaced from a position extending across the mitral valve orifice 16 by balloon dilation prior to delivery of the housing component 110 if desired.

Figure 14:
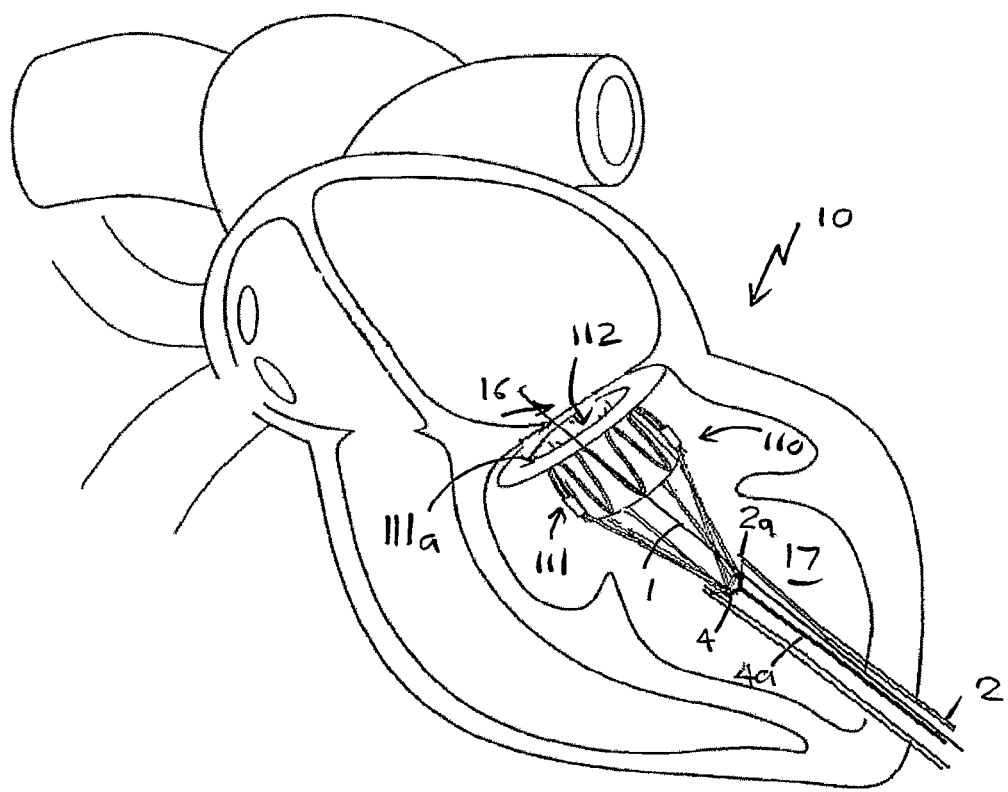
FIG. 14 is a schematic cross-sectional front elevation view of the heart to FIG. 12 with the housing component in a partially expanded state adjacent the mitral valve orifice.
Figure 15:
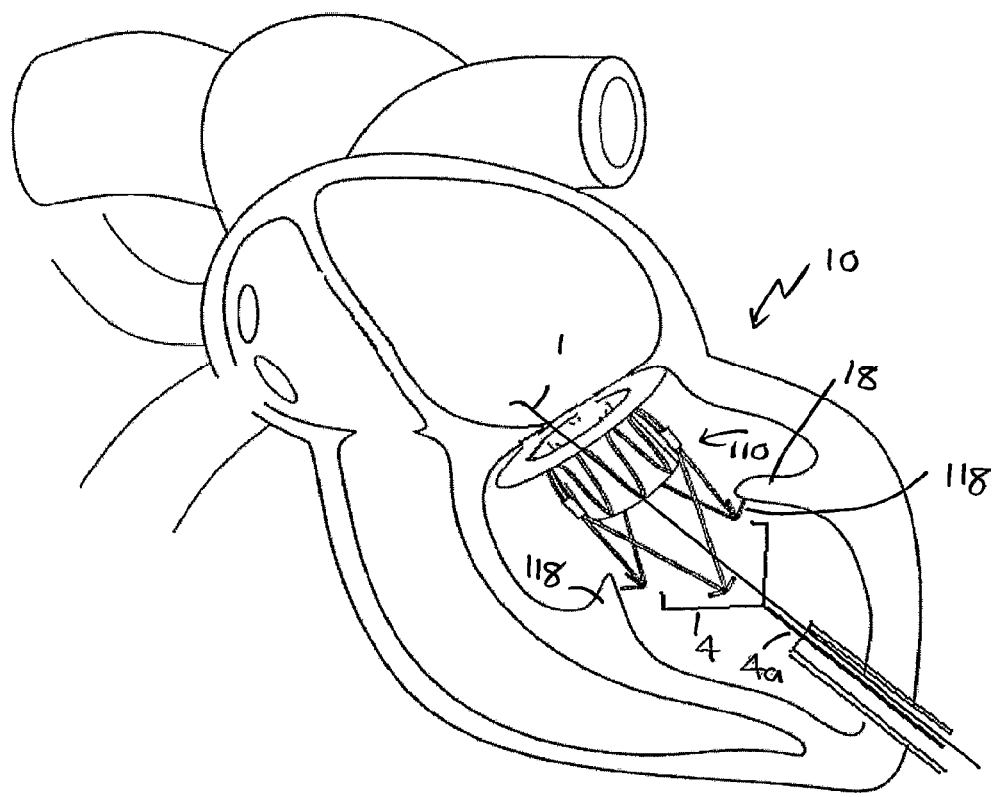
FIG. 15 is a schematic cross-sectional front elevation view of the heart of FIG. 12 with the guide wire withdrawn from the housing component.

The catheter 2 is then partly withdrawn whilst leaving the guide wire 1 and the housing component 110 in place, allowing the housing body 111 of the housing component 110 to expand as depicted in FIG. 14. At this stage, the ventricular prongs 118 are constrained by a restraining device 4 that is advanced with the housing component 110 alongside the guide wire 1. The restraining device 4 may be in the form of a wire clamp, wire lasso or similar formed on the end of an auxiliary wire 4a. The position of the housing component 110 is then fine tuned as required to position the housing body atrial end 111a adjacent the mitral valve orifice 16 providing communication with the housing passage 112. The catheter 2 is then further withdrawn and the restraining device 4 released, as depicted in FIG. 15, thereby allowing the housing component 110 to fully expand such that the ventricular prongs 118 engage the wall of the left ventricle 17 and/or papillary muscles 18 and/or other subvalvular tissue such as the chordae tendineae of the heart.

Figure 16:
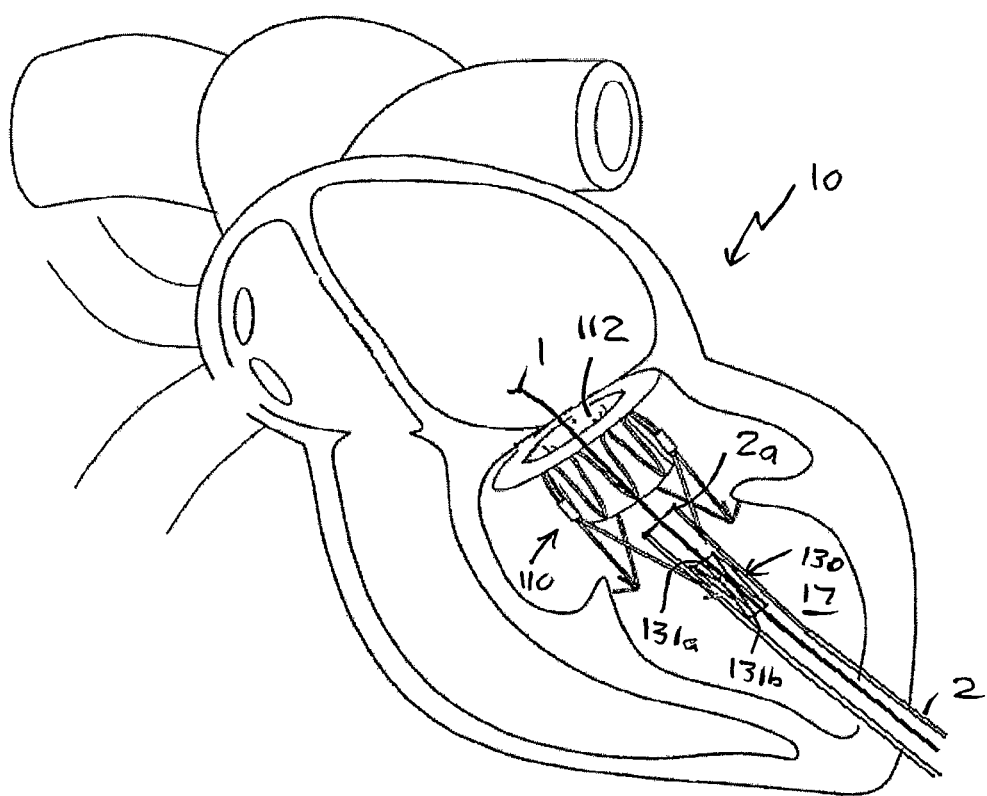
FIG. 16 is a schematic cross-sectional front elevation view of the heart of FIG. 12 with the valve component of the heart valve prosthesis of FIG. 1 advanced towards the end of the catheter.

Referring to FIG. 16, the valve component 130 of the heart valve prosthesis 100 is next collapsed and loaded into the catheter 2, with the valve body ventricular end 131b trailing the atrial end 131a.

Figure 17:
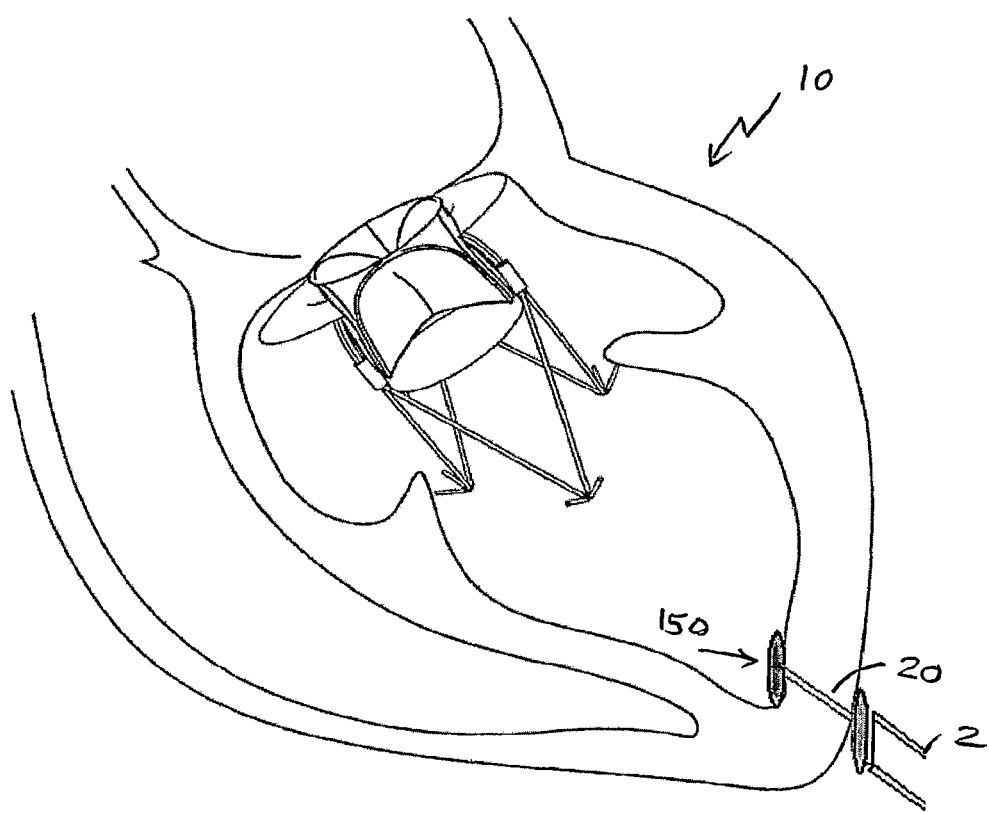
FIG. 17 is a schematic cross-sectional front elevation view of the heart of FIG. 12 with the heart valve prosthesis of FIG. 1 fully implanted.

The valve component 130 is advanced along the guide wire 1 towards the leading end 2a of the catheter 2 which itself is advanced to the ventricular end of the housing passage 112 within the housing component 110, ready for deployment of the valve component 130. Once the collapsed valve component 130 is located in the appropriate position within the housing passage 112, the catheter 2 is withdrawn, allowing the valve component 130 to elastically expand into engagement with the housing body frame 114 of the housing body 111, securing the valve component 130 to the housing body 111. The catheter 2 and guide wire 1 are then withdrawn from the left ventricle 17. Referring to FIG. 17, the puncture 20 in the apex 19 is then sealed by deploying a plug 150 in a known manner. The plug 150 will typically be deployed from the catheter 2 and may be in the form of a collapsible body formed of nitinol or any other suitable material. The catheter 2 and guide wire 1 are then fully withdrawn from the patient, leaving the assembled heart valve prosthesis 100 in position as depicted in FIG. 17, replacing the native mitral valve. The trans-apical approach described allows for more direct access to the mitral valve orifice than the venous approach described above in relation to FIGS. 6 to 11 which may provide access problems as a result of the tortuous nature of the access path through the venous system.

Figure 18:
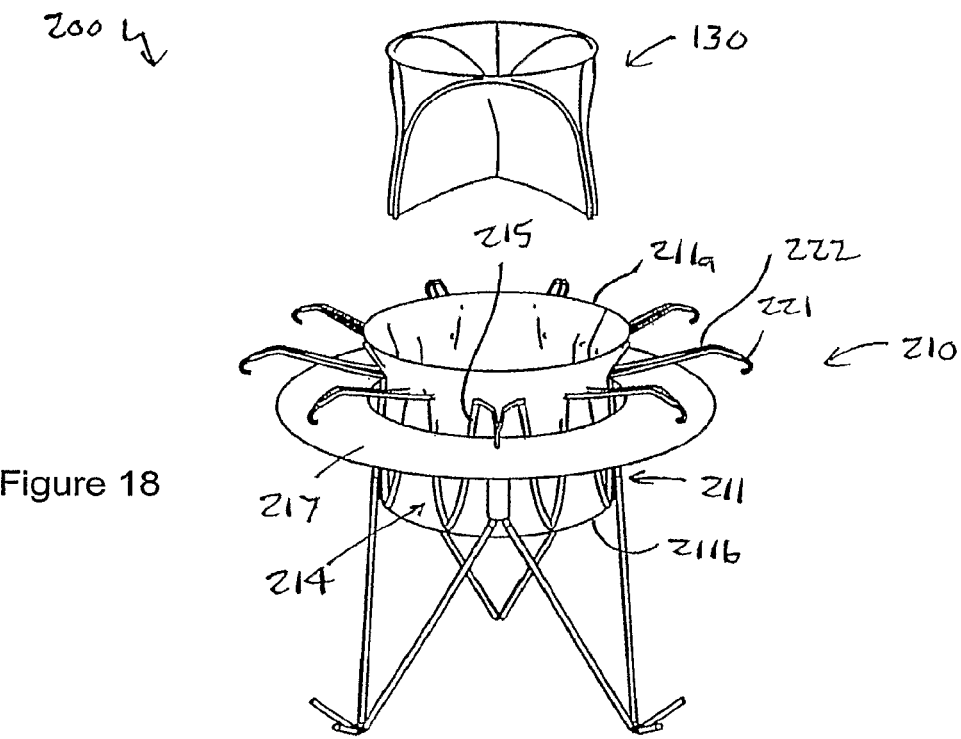
FIG. 18 is a perspective view of a heart valve prosthesis according to a second embodiment in a disassembled state.
Figure 19:
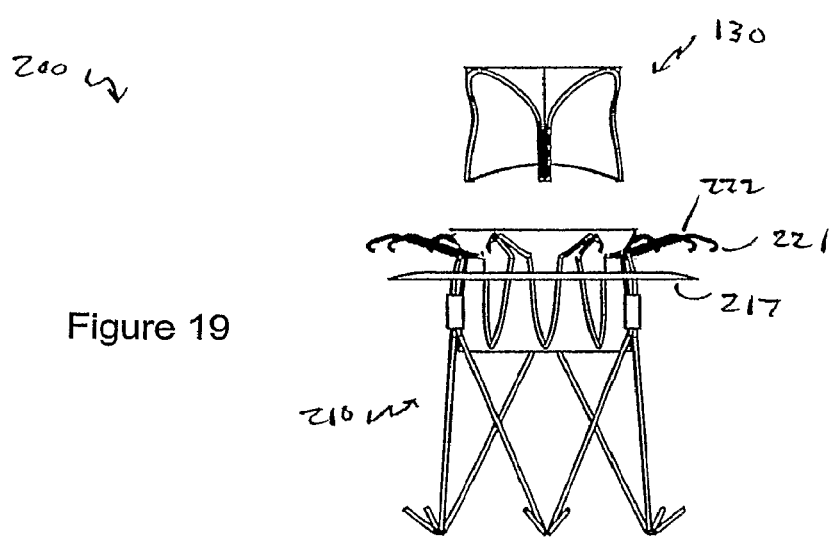
FIG. 19 is a front elevation view of the heart valve prosthesis of FIG. 18 in the disassembled state.

Referring to FIGS. 18 and 19 of the accompanying drawings, a second embodiment of a percutaneous heart valve prosthesis 200 is depicted. With the heart valve prosthesis 200, the valve component 130 is identical to that of the heart valve prosthesis 100 of the first embodiment described above.

The housing component 210 is similar to the housing component 110 of the first embodiment. Accordingly like or equivalent features adopt the same reference numerals as the housing component 110 of the first embodiment, increased by 100. A similar reference numeral system is applied for each of the hereinafter described embodiments. The housing component 210 has a housing body 211 that is intended to be located within the native mitral valve orifice 16 with the housing body atrial end 211a located within the left atrium 15 and the housing body ventricular end 211b located within the left ventricle 16. Accordingly, the flexible skirt 217 is located between the housing body atrial and ventricular ends 211a, 211b such that, in use, the flexible skirt 217 engages the native tissue surrounding the valve orifice 16 on the ventricular side. In the housing component 210, the anchoring mechanism further comprises a plurality of secondary or atrial prongs 221 secured to and spaced about the housing body atrial end 211a. Here the atrial prongs 221 are each secured to the housing body frame 214 by way of arms 222 that are each formed as a bent extension of individual housing body frame elements 215 of the housing body frame 214. The atrial prongs 221 extend over the delicate thin tissue immediately surrounding the valve orifice 16 so as to engage the muscular walls of the left atrium outside the valve orifice 16. The ends of the atrial prongs 221 are bent back to form generally radially inwardly directed hooks. The atrial prongs 222 assist in securing the housing body 211 in relation to the valve orifice, and particularly assist in preventing the housing body 211 from migrating into the left ventricle 17. The housing component 210 is otherwise substantially identical to the housing component 110 of the first embodiment.

Figure 20:
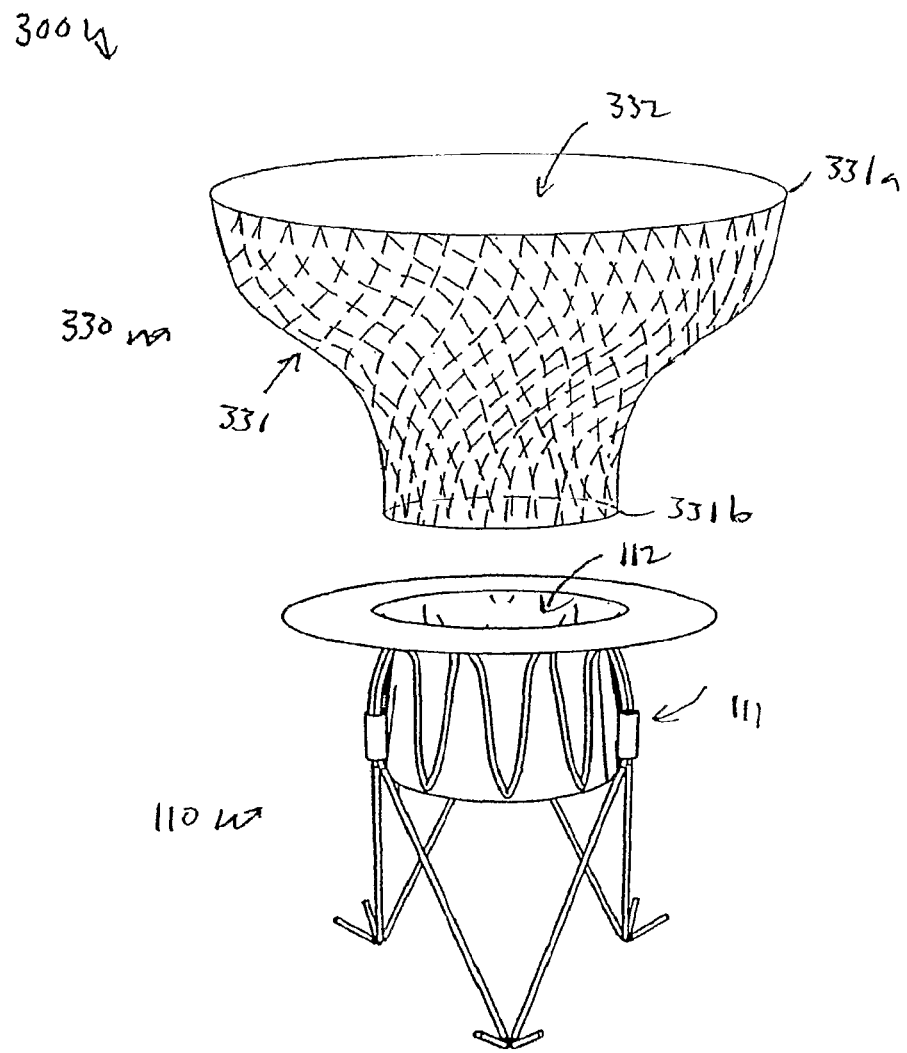
FIG. 20 is a perspective view of a heart valve prosthesis according to a third embodiment in a disassembled state.
Figure 21:
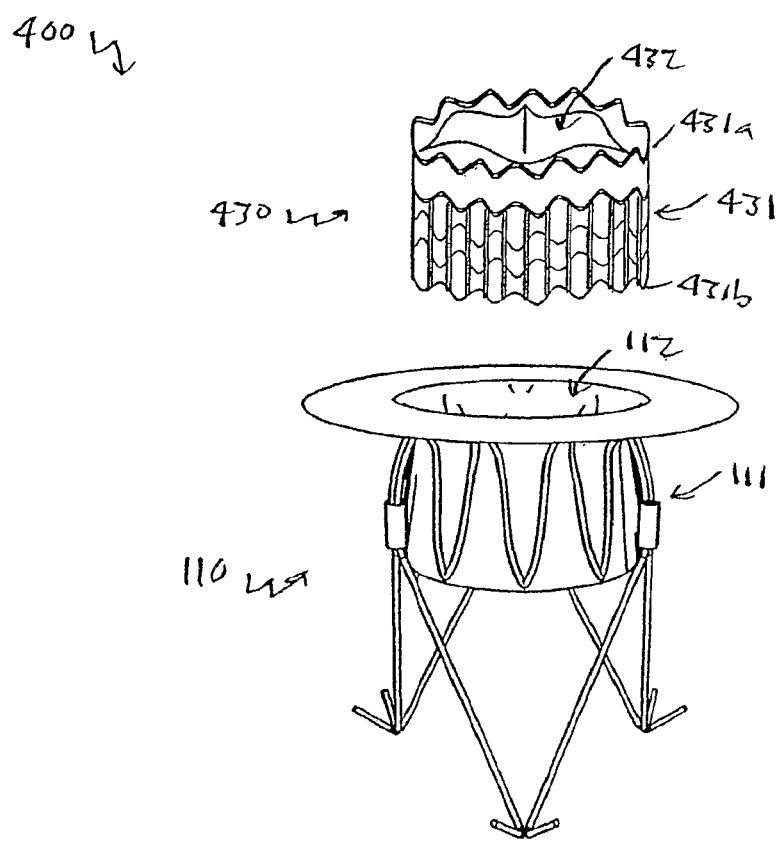
FIG. 21 is a perspective view of a heart valve prosthesis according to a fourth embodiment in the disassembled state.

Referring to FIG. 20, a third embodiment of a percutaneous heart valve prosthesis 300 is depicted. In this embodiment, the housing component 110 is identical to that of the heart valve prosthesis 100 of the first embodiment, whilst the valve element 330 is in the form of a percutaneously deliverable expandable stent valve. The valve body 331 of the valve component 330 may be either self-expanding or balloon expandable. The radial load applied to the housing body frame 114 when the valve body 331 is expanded within the housing passage 112 of the housing component 110 secures the valve body 331 to the housing body. The radial load is carried by the housing body 111 rather than the thin, delicate wall of the mitral valve orifice 16 as is the case with stent valves implanted directly into the mitral valve orifice 16. The valve body 331 is configured such that the valve body atrial end 331a protrudes beyond the housing body atrial end 111a and into the left atrium. The valve body 331 is of a generally tapered shape, with the valve body atrial end 331a being broader than the valve body ventricular end 331b such that the enlarged diameter of the valve body atrial end 331a expands into the left atrium 15, assisting in preventing movement of the heart valve prosthesis 380 downwards into the left ventricle. One or more flexible valve elements (not depicted) are secured to the valve body 331 and extend across the valve passage 332 for blocking blood flow to the valve passage 332 from the valve body ventricular end 331b toward the valve body atrial end 331a Referring to FIG. 21, a fourth embodiment of a heart valve prosthesis 400 again has the same housing component 110 as the heart valve prosthesis 100 of the first embodiment. In this embodiment, the valve component 430 is in the form of a percutaneously deliverable cylindrical stent valve. The valve body 431 is configured to be located substantially wholly within the housing passage 112 of the housing component 110 and may be secured to the housing body 111 solely by radial pressure following either balloon or self-expansion of the valve body 431. Alternatively, both the stent valve body 431 and housing body 111 could be provided with a double-taper in the same manner as depicted in FIGS. 3 and 4 to secure the valve body 431 within the housing passage 112. Alternatively, or additionally, the valve body 431 could be secured to the housing body 111 by clips or other suitable fasteners. One or more flexible valve elements (not depicted) are secured to the valve body 431 and extend across the valve passage 432 for blocking blood flow through the valve passage 432 from the valve body ventricular end 431b toward the valve body atrial end 431a.

Figure 22:
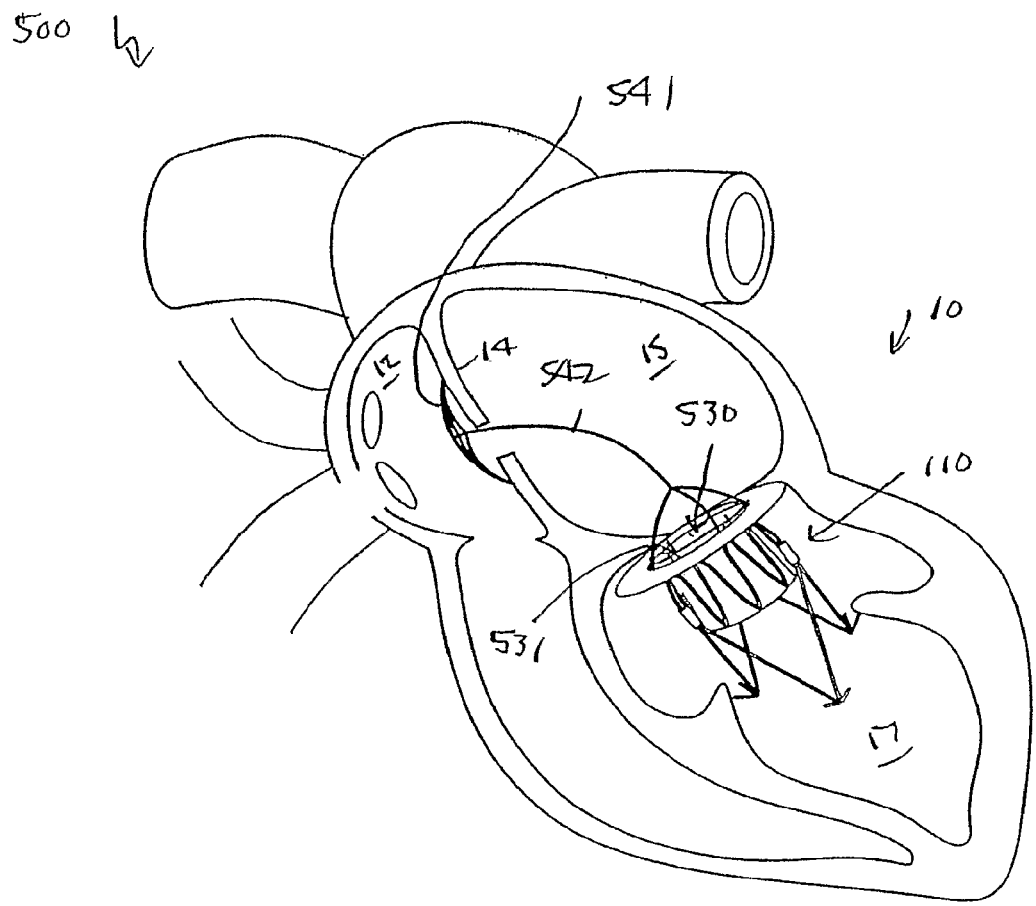
FIG. 22 is a perspective view of a heart valve prosthesis according to a fifth embodiment installed in a heart.

Referring to FIG. 22, a fifth embodiment of a percutaneous heart valve prosthesis 500 is depicted in an assembled state installed in a heart 10. The heart valve prosthesis 500 has a housing component 110 identical to the housing component of the heart valve prosthesis 100 of the first embodiment, and the housing component 110 is thus implanted in the same manner as described above. The valve component 530 is also identical to the valve component 130 of the first embodiment, with the addition of an anchor device 541 and flexible anchor line 542. The anchor line 542 connects the anchor device 541 to the valve body frame of the valve component 530. The anchor device 541 comprises an elastically collapsible anchor frame formed of elongate anchor frame elements, typically formed of the same material as the frame elements of the housing body and valve body. The anchor device 541 is elastically collapsible from a stable substantially flat plate-like configuration (as shown in FIG. 22) to an unstable elongate configuration for location within the catheter 2 during percutaneous delivery of the valve component 530. The anchor device 541 may conveniently be of the general form of the anchor device disclosed in International PCT Publication No. WO 2005/087140 to the present applicant, the entire contents of which are incorporated herein by cross-reference.

During percutaneous delivery of the valve component 530, the anchor device 541 is released from the end of the catheter 2 after release of the valve body 531 with the end of the catheter 2 retracted in the right atrium 12 adjacent the inter-atrial septum 14. Upon release of the anchor device 541 from the catheter 2, the anchor device 541 expands and acts as an anchor against the inter-atrial septum 14, anchoring the valve component 530 (and by virtue of the valve component's 530 fixation to the housing component 110, the entire heart valve prosthesis 500) against migration deeper into the left ventricle 17. It is also envisaged that the anchor device might alternately be permanently attached to the housing component 110, however, this would result in a significantly more complicated delivery procedure, given that the anchor device would tend to block the septal puncture 13, preventing delivery of the valve component through the same septal puncture. It is further envisaged that the anchor device 541 might be separate to both the housing component and valve component, being percutaneously delivered to the heart separately and following delivery of the valve component. The anchor device would then be secured to either the housing component or valve component within the heart. The anchor line 542 could either be delivered with the anchor device 541 and subsequently secured to the housing element/valve element or alternately the anchor line 542 could be delivered with the housing element/valve element and subsequently secured to the anchor device 541.

Figure 23:
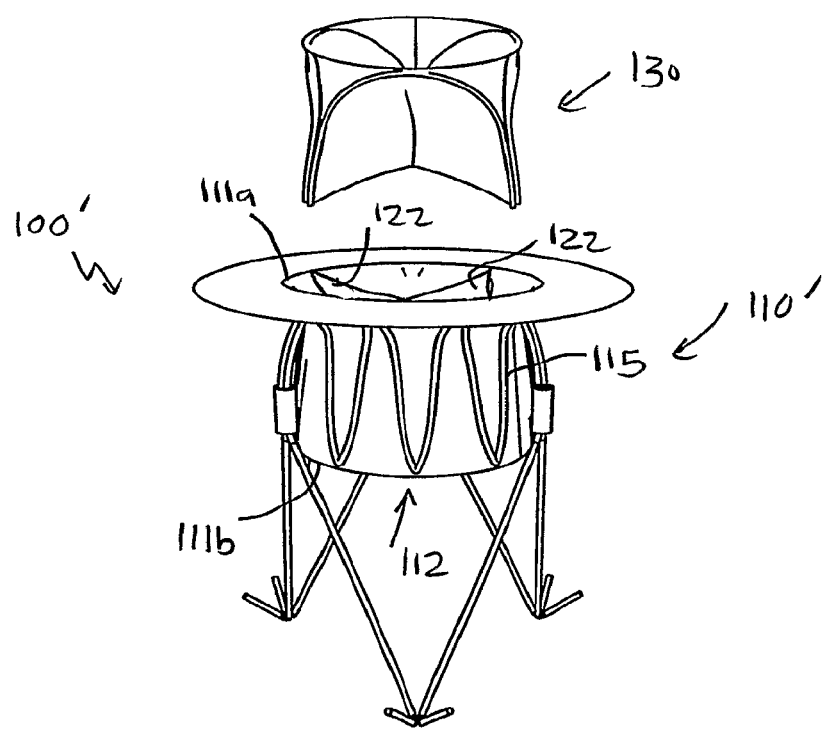
FIG. 23 is a perspective view of a heart valve prosthesis according to a sixth embodiment in a disassembled state.

Referring to FIG. 23, a sixth embodiment of a percutaneous heart valve prosthesis 100' is depicted in a disassembled state. The heart valve prosthesis 100' is identical to that of the first embodiment described above and depicted in FIG. 1 apart from the inclusion of a plurality of flexible temporary valve elements 122 in the housing component 110' secured to the housing body frame elements 115 so as to extend across the housing passage 112. The temporary valve elements 122 are configured to inhibit blood flow in the first direction through the housing passage 112 from the housing body ventricular end 111b towards the housing body atrial end 111a, whilst allowing blood flow in the opposing second direction. The temporary valve elements 122 serve to inhibit regurgitation of blood from the left ventricle 17 back into the left atrium 15 during the implantation procedure, following location of the housing component 110' until subsequent delivery of the valve component 130. Given that the temporary valve leaflets 122 are thus only operative for a relatively short time, they may be quite simple in configuration and be made from simple flexible synthetic materials. The prosthesis 100' may be implanted utilizing any of the procedures discussed above, with the valve component 130 simply pushing aside the temporary valve leaflets 122 when expanded into position within the housing passage 112. The temporary valve leaflets 122 remain sandwiched between the valve component 130 and the housing wall 116.

In a further embodiment (not depicted) the housing component of the percutaneous heart valve prosthesis has a housing body in the form of an expandable stent structure having a central portion configured to be located within the native mitral valve orifice, an atrial end portion configured to be located within the left atrium and an opposing ventricular portion configured to be located within the left ventricle. When located in position, the central portion of the housing body is only partly expanded to a diameter not exceeding that of the native mitral valve orifice, so as not to place any significant radial pressure loads on the wall of the valve orifice. The opposing atrial and ventricular portions of the housing body are further expanded beyond the diameter of the valve orifice so as to effectively "sandwich" the wall of the native mitral valve orifice between the atrial and ventricular portions of the housing body, thereby fixing the housing body in relation to the valve orifice. Any of various forms of the valve component could then be fixed within the housing passage defined by the housing body.

Various other forms of securing the various heart valve prostheses described above are also envisaged. For example, the valve component may be configured with ventricular or atrial prongs to assist in directly fixing the valve component to the structure of the heart. The valve body and housing body may also be tapered so as to act as a plug that cannot migrate through the heart valve orifice, with an anchoring mechanism being located on that side of the valve orifice through which the narrower end of the housing body and valve body protrude. For example, with the heart valve prosthesis 500 of the fifth embodiment described above in relation to FIG. 22, the atrial end of both the valve body and housing body could be narrower than the valve orifice and the ventricular end of the valve body and housing body, with the anchor device 541 and anchor line 542 acting to retain the heart valve prosthesis partly within the heart valve orifice in a plugged state. In such an arrangement, the flexible skirt 117 of the housing component would be located partway between the atrial and ventricular ends of the housing body. It is also envisaged that the valve component may also be provided with a flexible skirt similar, and additional to or in place of, the flexible skirt 117 of the housing component 110.

Whilst the various two component heart valve prosthesis described above each relate to a mitral valve prosthesis, the two component prosthesis concept is also applicable to each of the remaining heart valves, being the tricuspid valve and the semilunar valves (that is, the pulmonary valve and the aortic valve).

A seventh embodiment of a two component heart valve prosthesis, in the form of an aortic heart valve prosthesis 600, and an associated aortic heart valve replacement procedure will now be described with reference to FIGS. 24 through 29.

Figure 24:
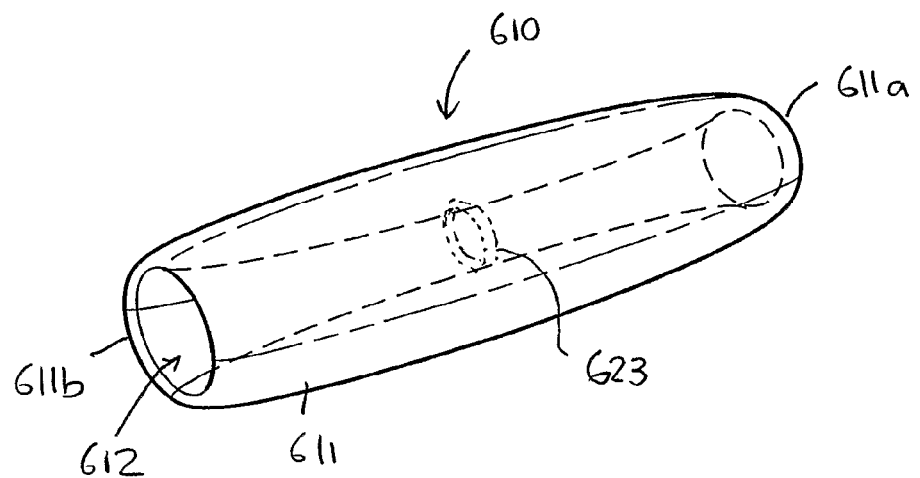
FIG. 24 is a perspective view of the housing component of a heart valve prosthesis according to a seventh embodiment.
Figure 25:
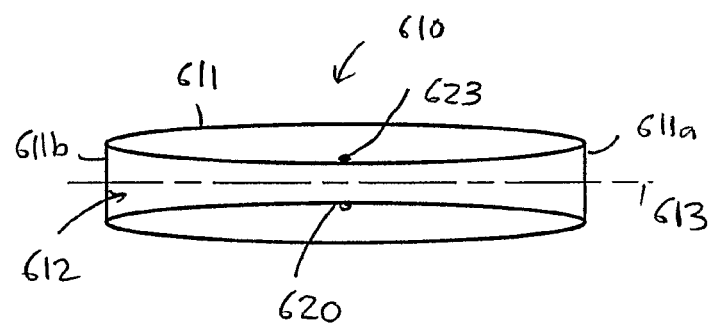
FIG. 25 is a cross-sectional front elevation view of the housing component of FIG. 24.

Referring firstly to FIGS. 24 and 25, the housing component 610 of the aortic valve prosthesis 600 comprises a generally tubular housing body 611 that has a housing body first end 611a, a housing body second end 611b and a housing passage 612 extending between the housing body first and second ends 611a, 611b along a longitudinal housing axis 613. The housing passage 612 is double tapered, with the housing passage 612 being wider at the housing body first and second ends 611a, 611b than in the central neck region 620 of the housing passage 612. This double tapering of the housing passage 612 assists in positioning and retaining the valve component 630 as will be discussed further below. The housing component 610 is sized and shaped to be located within the ascending aorta 22 of the patient's heart 10 in the position of the native aortic valve.

The housing body 611 is here in the form of an elastically compressible, flexible biocompatible material. Particularly preferred materials for construction of the housing body 611 include silicone and other bio-stable polymers. Alternatively, the housing body 611 could be in the form of a covered wire mesh stent. Persons skilled in the art will appreciate that many other suitable materials may alternatively be utilized. The housing component 610 is elastically collapsible from a stable expanded state, as depicted in FIGS. 24 and 25, into an unstable collapsed state extending along the housing longitudinal axis 613 to allow delivery of the housing component 610, typically percutaneously, by catheter. The housing component 610 may be forced into the unstable collapsed state for delivery by the application of radial compressive force. The housing component 610 may include a marker 623, in the form of a small metallic ring. The marker 623 may be integrally moulded with the housing body 612 or otherwise inserted into the housing passage 611 prior to implantation. The marker 623 extends about the housing passage 612 and is adapted to be visible on fluoroscopic or X-ray imaging equipment so as to facilitate doctors and surgeons identifying the position, orientation and location of the housing component 610, which may be otherwise invisible to these imaging techniques when the housing body 611 is formed of a polymeric material.

Figure 28:
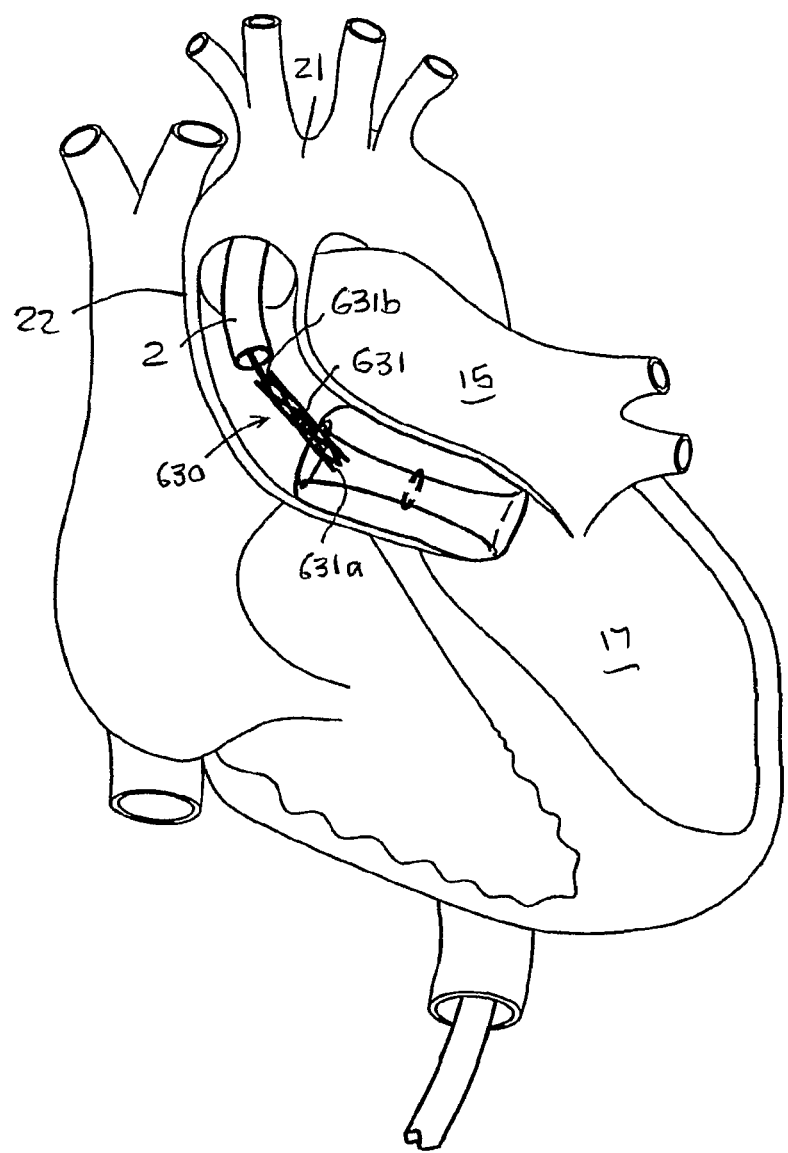
FIG. 28 is a schematic cross-sectional front elevation view of the heart of FIG. 26 with the valve component of the heart prosthesis of the sixth embodiment advanced beyond the end of the catheter.
Figure 29:
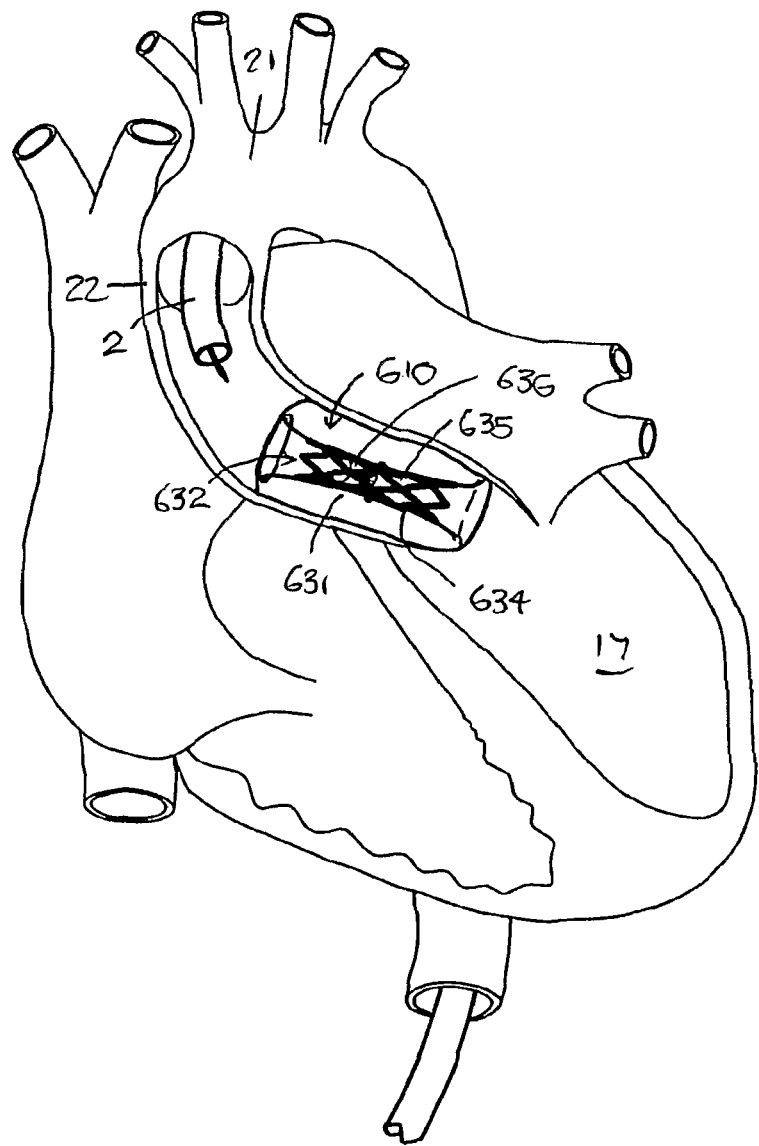
FIG. 29 is a schematic cross-sectional front elevation view of the heart of FIG. 26 with the heart valve prosthesis of the sixth embodiment fully implanted.

In the particular arrangement depicted in FIGS. 28 and 29, the valve component 630 comprises a tubular valve body 631 that has a valve body first end 631a, a valve body second end 631b, and a valve passage 632 extending between the valve body first and second ends 631a, 631b along a longitudinal valve axis. In the arrangement depicted, the valve body 631 is formed of a valve body frame 534 that has a stent structure formed of elongate elastic valve body frame elements 635. The valve body frame elements 635 are each typically formed of a wire of super elastic shape memory material such as nitinol, stainless steel, other titanium alloys and/or cobalt, chromium, molybdenum. Other suitable relatively rigid yet elastic metal alloys or non-metallic materials may alternatively be utilized as desired. The valve body frame elements 635 are generally formed with a diamond pattern as is typical with stent structures.

A plurality of flexible valve elements 636 are secured to the valve body frame elements 635, typically by suturing. Rather than being secured directly to the valve body frame elements 635, the valve elements 636 may be secured to a sub-frame of the valve body frame 634 formed of three elongate elastic elements that are each formed into an arch and formed of a wire of superelastic shape memory material, typically being the same as that of the valve body frame elements 635. The sub-frame may be generally of the same form as the housing body frame 134 of the valve component 130 of the mitral valve prosthesis 100 of the first embodiment. The sub-frame in this case would be secured to the valve body frame 634, typically by suturing.

The valve elements 636 may again be formed of a suitable flexible biological material, such as pericardial material including bovine pericardium or kangaroo pericardium. Alternatively the valve elements 636 may be formed of a suitable flexible non-biological material. The valve elements 636 are configured such that they extend across the valve passage 632 in a manner that they block blood flow in a first direction to the valve passage 632 from the valve body second end 631b towards the valve body first end 631a, whilst allowing blood flow in an opposing second direction. The entire valve component 630 is collapsible from a stable expanded state into a collapsed state extending along the valve longitudinal axis 633 to allow delivery of the valve component 630, typically percutaneously by catheter. The stent structure of the valve body frame 634 may be elastically collapsible, such that it is self-expanding when released, or may otherwise be expandable by balloon.

The valve component 630 may alternatively be of the same construction as the valve component 130 described above in relation to the first embodiment depicted in FIGS. 1 and 2, or may take any of various other forms including that of the valve component 430 of the heart valve prosthesis 400 of the fourth embodiment described above in relation to FIG. 15.

Replacement of a failed or failing aortic valve by implantation of the aortic valve prosthesis 600 of the sixth embodiment above using a percutaneous arterial approach will now be described with reference to FIGS. 26 through 29. The arterial system of the patient to be treated is firstly accessed by a puncture providing access to the femoral artery.

Figure 26:
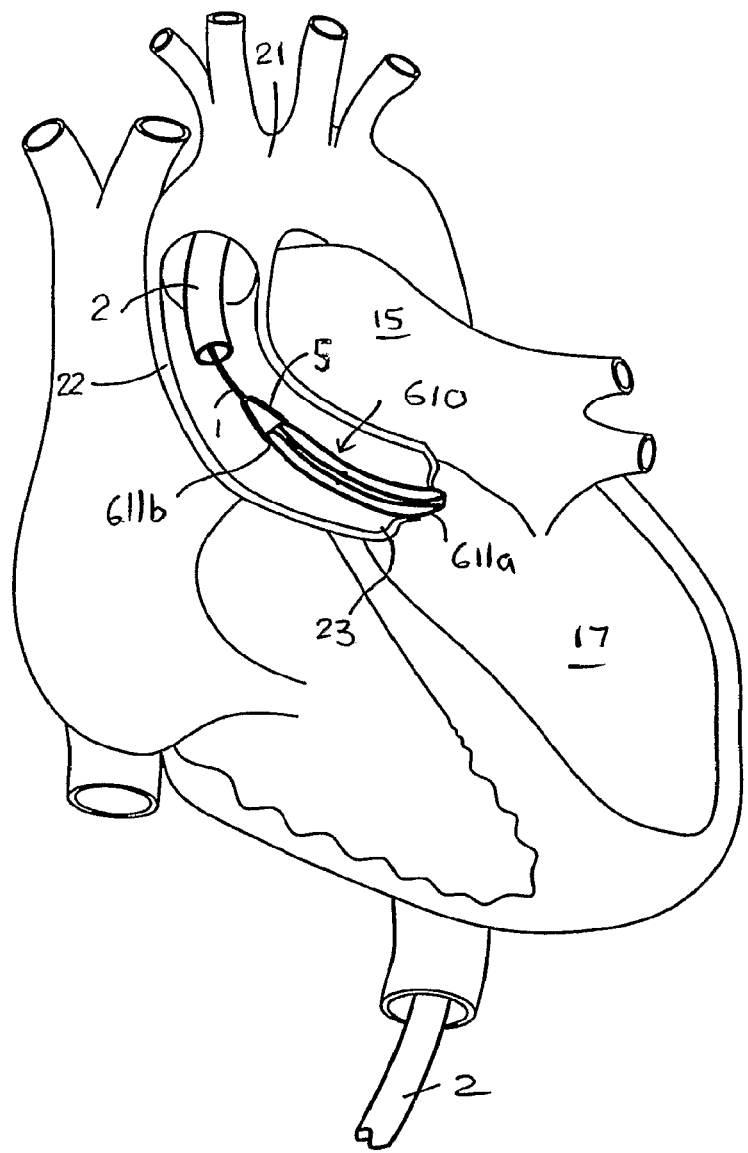
FIG. 26 is a schematic cross-sectional front elevation view of a heart depicting the housing component of FIG. 24 advanced beyond the end of a catheter located in the ascending aorta.

Referring to FIG. 26, a guide wire 1, typically having a diameter of approximately 0.85 mm to 1.7 mm, is inserted through the puncture and advanced along the femoral artery to the descending aorta, through the aortic arch 21 and into the ascending aorta 22. A catheter 2, typically having a diameter of about 20 to 24 F (6.77 mm to 8.0 mm) is then advanced over the guide wire 1 and into the ascending aorta 22. The housing component 610 of the aortic valve prosthesis 600 is radially compressed into its collapsed state and fed into the catheter 2 with the housing body second end 611b trailing the housing body first end 611a. The housing component 610 is then delivered percutaneously by being advanced along the guide wire 1 through the catheter 2. A restraining device 5 at the leading end of the guide wire 1 restrains the housing component 610 in its radially compressed and collapsed state as the guide wire 1 is further advanced beyond the leading end 2a of the catheter towards the lower end of the ascending aorta 22 which forms the native aortic valve orifice 23. The restraining device 5 is released once the housing component 610 is in position with the housing body first end 611a located adjacent the lower end of the ascending aorta 22 and the housing body second end 611b extending towards the aortic arch 21. The marker 623 assists in ensuring correct placement.

Figure 27:
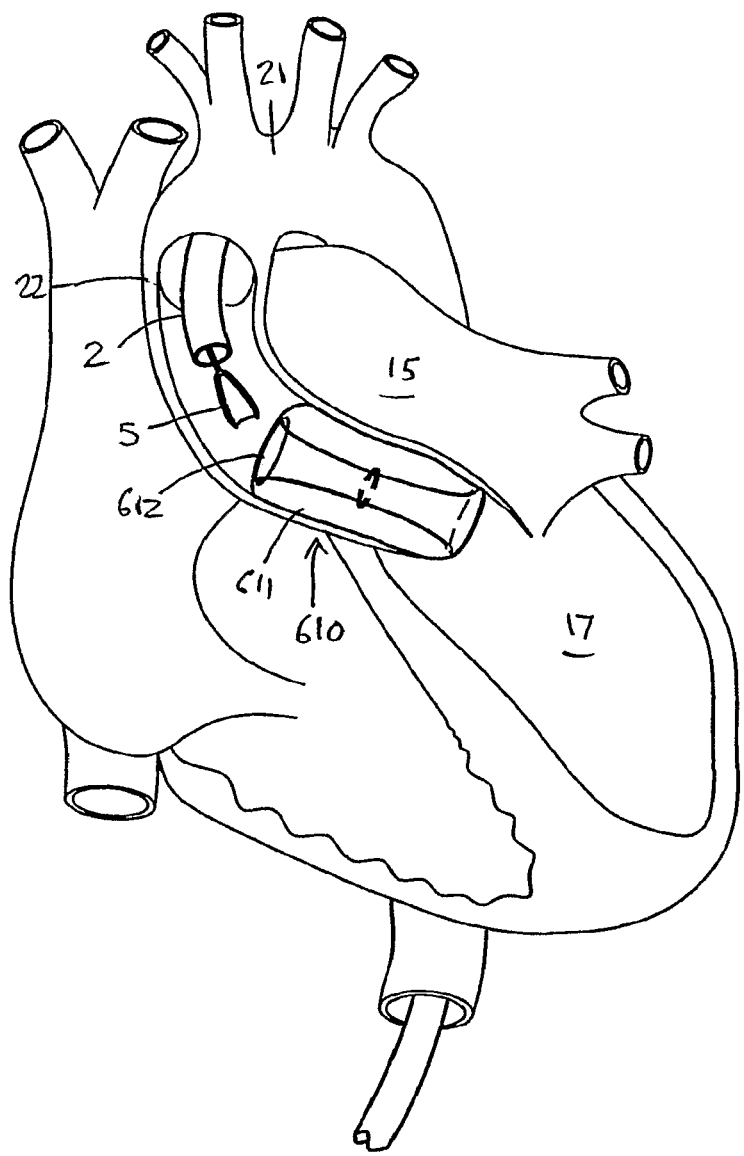
FIG. 27 is a schematic cross-sectional front elevation view of the heart of FIG. 26 with the housing in the expanded state in the ascending aorta.

Once the housing component 610 is released, it elastically expands into its expanded state, engaging the walls of the ascending aorta 22 so as to secure the housing component 610 within the ascending aorta 22 as depicted in FIG. 27. Radial expansion of the housing component 610 opens the housing passage 612. The radial expansion of the housing component 610 also presses the native valve leaflets against the wall of the ascending aorta 22. The elastic nature of the housing body 611 provides for an effective seal between the housing body 611 and the wall of the ascending aorta 22, thereby eliminating paravalvular leaks.

Referring to FIG. 28, the valve component 630 is next collapsed into its collapsed state and fed into the catheter 2 with the valve body second end 631b trailing the valve body first end 631a. The valve component 630 is advanced along the guide wire 1 towards the leading end 2a of the catheter 2. The valve component 630 is again restrained by the restraining device 5 as the valve component 630 is advanced beyond the leading end 2a of the catheter and into the housing passage 612 of the housing component 610. The valve component 630 is advanced into its appropriate position within the housing passage 612. This position may be conveniently determined utilizing the marker 623 of the housing component 610. A further marker may be provided on the valve component 630 if desired, although the valve body 631 will generally already be visible on fluoroscopic or X-ray imaging equipment, given that it is formed of metallic wire. The valve component 630 is expanded into its expanded state with the valve body first end 631a being located towards the housing body first end 611a and the valve body second end 631b located towards the housing body second end 611b.

If the valve body 631 is of a self-expanding form, release from the restraining device 3 will result in the valve component self-expanding into engagement with the wall of the housing body 611. Alternatively, the valve body 631 may be expanded by balloon catheterization if the valve body is of a non-self-expanding configuration. It is also envisaged that, in configurations where the shape memory characteristics of the nitinol wire forming the valve body frame 634 have been utilized to collapse the valve body 631 for delivery by catheter, the restraining device 5 may apply heat to the valve body frame 634 so as to heat the valve body frame elements 635 and thereby radially expand the valve body 631 into its stable expanded state.

When the valve body 631 is expanded, engaging the walls of the housing body 611, the double-tapered configuration of the housing passage 612 acts to secure the valve component 630 within the housing passage 612. Biocompatible adhesives could additionally or alternatively be utilized to secure the valve body 631 to the housing body 611. The housing body 611 could also be further secured to the wall of the ascending aorta 23 with biocompatible adhesives. Such adhesives could also be utilized in the various other embodiments described. The catheter 2 and guide wire 1 are then withdrawn from the patient, leaving the assembled heart valve prosthesis 610 in position as depicted n FIG. 29. Blood flow from the left ventricle 17 into the ascending aorta 22 is provided for through the valve elements 636 whilst the same valve elements 636 prevent back flow from the ascending aorta 22 into the left ventricle 17.

It is also envisaged that the aortic valve prosthesis 600 of the sixth embodiment may be implanted using a surgical or percutaneous trans-apical approach equivalent to the to mitral valve replacement trans-apical approach described above in relation to FIGS. 12 through 17. In such an approach, access would again be provided to the left ventricle (and ascending aorta) via a puncture in the apex of the left ventricle.

Persons skilled in the art will also appreciate various other possible modifications to the heart valve prosthesis and associated methods of implantation.

What is claimed is:

1. A method of replacing a native atrioventricular valve of a heart of a patient, the method comprising:
    delivering a housing component in a radially compressed state through the vasculature of the patient to the native atrioventricular valve, wherein the housing component comprises a housing body having an atrial end, a ventricular end, and a housing passage extending from the atrial end to the ventricular end, the housing component further comprising a plurality of ventricular prongs secured to and spaced about the housing body and an atrial anchoring mechanism secured to the housing body;
    radially expanding the housing component at the native atrioventricular valve to a radially expanded state such that the housing body is located within the native atrioventricular valve, the atrial anchoring mechanism extends over and engages tissue surrounding the native atrioventricular valve within the atrium of the heart communicating with the native atrioventricular valve, and the ventricular prongs engage native tissue structure of the heart within the ventricle of the heart communicating with the native atrioventricular valve orifice;
    delivering a valve component in a radially compressed state through the vasculature of the patient to the native atrioventricular valve, the valve component comprising a valve body having a valve passage extending therethrough and three leaflets made from pericardium secured to the valve body; and
    radially expanding the valve component to a radially expanded state within the housing component such that the three leaflets allow blood to flow from the atrium to the ventricle through the valve body and block the flow of blood through the valve body from the ventricle to the atrium.

2. The method of claim 1, wherein the valve component is expanded within the housing component after the housing component is radially expanded.

3. The method of claim 1, wherein:
    radially expanding the housing component comprises deploying the housing component from a catheter, thereby allowing the housing component to self-expand from its radially compressed state to its radially expanded state; and
    radially expanding the valve component comprises deploying the valve component from a catheter, thereby allowing the valve component to self-expand from its radially compressed state to its radially expanded state.

4. The method of claim 3, wherein the housing component and the valve component are deployed from the same catheter.

5. The method of claim 3, wherein the housing component and the valve component are deployed from different catheters.

6. The method of claim 3, further comprising, prior to delivering the housing component and the valve component, inserting a first catheter through the venous system of the patient to position a distal end of the first catheter in the heart, wherein delivering the housing component comprises delivering the housing component via a second catheter that extends through the first catheter, and wherein deploying the housing component comprises deploying the housing component from a distal end of the second catheter.

7. The method of claim 6, wherein delivering the valve component comprises delivering the valve component via a third catheter that extends through the first catheter, and wherein deploying the valve component comprises deploying the valve component from a distal end of the third catheter.

8. The method of claim 1, wherein the atrial anchoring mechanism comprises a plurality of atrial prongs.

9. The method of claim 8, wherein the plurality of atrial prongs engages a wall of the atrium when the housing component is in its radially expanded state.

10. The method of claim 1, wherein the ventricular prongs are each secured to the housing body by one or more legs extending from the ventricular end of the housing body.

11. The method of claim 1, wherein the valve component is deployed wholly within the passage of the housing component.

12. The method of claim 1, wherein the housing body comprises a metal frame and a polyester flexible wall sutured to the metal frame.

13. The method of claim 1, wherein the housing component further comprises one or more flexible temporary valve elements secured to the housing body and extending across the housing passage for inhibiting blood flow from the ventricle to the atrium through the housing passage and allowing blood flow from the atrium to the ventricle through the housing passage prior to delivery of the valve component.

14. A method of replacing a native atrioventricular valve of a heart of a patient, the method comprising:
    delivering a housing component in a radially compressed state through the vasculature of the patient to the native atrioventricular valve, wherein the housing component comprises a housing body having an atrial end, a ventricular end, and a housing passage extending from the atrial end to the ventricular end, the housing component further comprising a plurality of ventricular prongs secured to and spaced about the housing body and an annular sealing element connected to the atrial end, wherein the annular sealing element is made of polyester and is reinforced with wire;

radially expanding the housing component at the native atrioventricular valve to a radially expanded state such that the housing body is located within the native atrioventricular valve and the ventricular prongs to engage sub-valvular tissue of the heart within the ventricle of the heart communicating with the native atrioventricular valve orifice, and the annular sealing element extends radially outwardly from the atrial end of the housing body over tissue surrounding the native atrioventricular valve orifice within the atrium of the heart communicating with the native atrioventricular valve orifice;

delivering a valve component in a radially compressed state through the vasculature of the patient to the native atrioventricular valve, the valve component comprising a valve body having a valve passage extending therethrough and three leaflets made from pericardium secured to the valve body; and radially expanding the valve component to a radially expanded state within the housing component such that the three leaflets allow blood to flow from the atrium to the ventricle through the valve body and block the flow of blood through the valve body from the ventricle to the atrium;

wherein the expanded valve component has an inflow end portion that protrudes into the atrium of the heart communicating with the native atrioventricular valve.

15. The method of claim 14, wherein the housing component further comprises an atrial anchoring mechanism that extends over and engages tissue surrounding the native atrioventricular valve within the atrium of the heart when the housing component is in its radially expanded state.

16. The method of claim 15, wherein the atrial anchoring mechanism comprises atrial prongs that engages a wall of the atrium when the housing component is in its radially expanded state.

17. The method of claim 14, wherein:
radially expanding the housing component comprises deploying the housing component from a first catheter, thereby allowing the housing component to self-expand from its radially compressed state to its radially expanded state; and
radially expanding the valve component comprises deploying the valve component from a second catheter, thereby allowing the valve component to self-expand from its radially compressed state to its radially expanded state.

18. The method of claim 17, wherein deploying the housing component from the first catheter allows the ventricular prongs to self-expand into engagement with the sub-valvular tissue of the heart.

19. The method of claim 14, wherein the ventricular prongs are each secured to the housing body by one or more legs extending from the ventricular end of the housing body.

20. A method of replacing a native mitral valve of a heart of a patient, the method comprising:
inserting a first catheter through the venous system of the patient to position a distal end of the first catheter in the heart;
delivering a housing component in a radially compressed state to the native mitral valve via a second catheter extending through the first catheter, wherein the housing component comprises a housing body having an atrial end, a ventricular end, a housing passage extending from the atrial end to the ventricular end, a housing body frame and a flexible polyester wall sutured to the housing body frame, the housing component further comprising a plurality of ventricular prongs secured to and spaced about the housing body frame and a plurality of atrial prongs secured to the housing body frame, wherein the housing body frame, the ventricular prongs and the atrial prongs are made of a shape memory alloy;
deploying the housing component from the first catheter to allow the housing component to self-expand from the radially compressed state to a radially expanded state such that the housing body is located within the native mitral valve, the atrial prongs extends over and engage tissue surrounding the native mitral valve within the left atrium of the heart, and the ventricular prongs engage native tissue structure of the heart within the left ventricle of the heart;
after deploying the housing component, delivering a valve component in a radially compressed state to the native mitral valve via a third catheter extending through the first catheter, the valve component comprising a valve frame having a valve passage extending therethrough and three leaflets made from pericardium secured to the valve frame, wherein the valve frame is made of a shape memory alloy; and
deploying the valve component from the third catheter to allow the valve component to self-expand from the radially compressed state to a radially expanded state within the housing component such that the three leaflets allow blood to flow from the atrium to the ventricle through the valve body and block the flow of blood through the valve body from the ventricle to the atrium.

21. The method of claim 14, wherein the ventricular prongs have end portions with tips that point toward the atrial end of the housing component.

22. The method of claim 14, wherein the housing component comprises a metal frame and a flexible wall made of polyester sutured to the metal frame, and the polyester annular sealing element is sutured to the polyester flexible wall.

* * * * *